(12) United States Patent
Johnson et al.

(10) Patent No.: US 11,779,573 B2
(45) Date of Patent: Oct. 10, 2023

(54) CRYSTALLINE FORMS OF COMPOUNDS FOR PREVENTING OR TREATING SENSORY HAIR CELL DEATH

(71) Applicant: University of Washington, Seattle, WA (US)

(72) Inventors: Graham Johnson, Sanbornton, NH (US); Edwin Aret, Almere (NL); Alexei Tchesnokov, Germantown, WI (US)

(73) Assignee: University of Washington, Seattle, WA (US)

( * ) Notice: Subject to any disclaimer, the term of this patent is extended or adjusted under 35 U.S.C. 154(b) by 54 days.

(21) Appl. No.: 16/642,877

(22) PCT Filed: Aug. 31, 2018

(86) PCT No.: PCT/US2018/049113
§ 371 (c)(1),
(2) Date: Feb. 27, 2020

(87) PCT Pub. No.: WO2019/046731
PCT Pub. Date: Mar. 7, 2019

(65) Prior Publication Data
US 2020/0345705 A1    Nov. 5, 2020

Related U.S. Application Data

(60) Provisional application No. 62/553,568, filed on Sep. 1, 2017.

(51) Int. Cl.
| A61K 31/439 | (2006.01) |
| A61K 31/702 | (2006.01) |
| C07D 495/18 | (2006.01) |

(52) U.S. Cl.
CPC .......... *A61K 31/439* (2013.01); *A61K 31/702* (2013.01); *C07D 495/18* (2013.01); *C07B 2200/13* (2013.01)

(58) Field of Classification Search
CPC .. A61K 31/439; A61K 31/702; C07D 495/18; C07B 2200/13
USPC .......................................................... 514/61
See application file for complete search history.

(56) References Cited

U.S. PATENT DOCUMENTS

| 9,493,482 B2 | 11/2016 | Simon et al. |
| 2009/0318450 A1* | 12/2009 | Hangauer, Jr. ............ A61P 3/04 544/124 |
| 2016/0229869 A1 | 8/2016 | Simon et al. |
| 2016/0326186 A1 | 11/2016 | Simon et al. |
| 2018/0022756 A1 | 1/2018 | Simon et al. |

FOREIGN PATENT DOCUMENTS

| WO | 2016/127123 A3 | 8/2016 |
| WO | 2019/046731 A1 | 3/2019 |

OTHER PUBLICATIONS

Elder et al. (Journal of Pharmaceutical Sciences, vol. 99, No. 7, Jul. 2010, 2948-2961).*
International Search Report and Written Opinion, mailed Nov. 30, 2018, in Application No. PCT/US2018/49113, filed Aug. 31, 2018, 8 pages.
Extended European Report dated Mar. 5, 2021, issued in corresponding European Application No. EP 18849724, filed Aug. 31, 2018, 6 pages.
Australian Examination Report dated Aug. 9, 2022, issued in corresponding Application No. AU2018325267, filed Aug. 31, 2018, 3 pages.
Chinese Office Action dated Aug. 26, 2022, issued in corresponding Application No. 201880070449.1, filed Aug. 31, 2018, 16 pages.
Office Action dated Sep. 6, 2022, issued in corresponding Japanese Application No. 2020-512351, filed Aug. 31, 2018, 15 pages.
Office Action dated Jan. 17, 2023, issued in corresponding European Application No. 18849724.2, filed Aug. 31, 2018, 4 pages.
Office Action dated Feb. 14, 2023, issued in corresponding Chinese Application No. 2018800704491, filed Aug. 31, 2018, 19 pages.
Office Action dated May 25, 2023, issued in corresponding Chinese Application No. 2018800704491, filed Aug. 31, 2018, 13 pages.

* cited by examiner

*Primary Examiner* — Layla D Berry
(74) *Attorney, Agent, or Firm* — Christensen O'Connor Johnson Kindness PLLC

(57) ABSTRACT

Described herein is (4R,7S)-2-(3-(4-chlorophenyl)ureido)-9-methyl-5,6,7,8-tetrahydro-4H-4,7-epiminocyclohepta[b]thiophene-3-carboxamide mesylate, including crystalline forms and solvates thereof.

16 Claims, 8 Drawing Sheets

CRYSTALLINE FORMS OF COMPOUNDS FOR PREVENTING OR TREATING SENSORY HAIR CELL DEATH

CROSS-REFERENCE

This application claims benefit of U.S. Provisional Application No. 62/553,568, filed on Sep. 1, 2017, which is herein incorporated by reference in its entirety.

BACKGROUND

Aminoglycosides are clinically used drugs that cause dose-dependent sensorineural hearing loss (Smith et al., New Engl J Med, (1977) 296:349-53) and are known to kill hair cells in the mammalian inner ear (Theopold, Acta Otolaryngol (1977) 84:57-64). In the U.S. over 2,000,000 people receive treatment with aminoglycosides per year. The clinical efficacy of these antibiotics in treating drug-resistant bacterial infections and their low cost account for their continued worldwide use despite their known ototoxicity liability. The incidence of vestibulotoxic effects of such drugs on patient populations has been less well studied. Estimates range between 3% and 6% with continued reports in the literature of patients with aminoglycoside induced vestibulotoxicity (Dhanireddy et al., Arch Otolarngol Head Neck Surg (2005) 131:46-48). Other clinically important and commonly used drugs also have documented ototoxic effects, including cisplatin (Allen, et al., Otolaryngol Head Neck Surg (1998) 118:584-588), loop diuretics (Greenberg, Am J Med Sci, (2000) 319:10-24), antimalarial sesquiterpene lactone endoperoxides (i.e., artemesinins) (Toovey and Jamieson, Trans R Soc Trop Med Hyg (2004) 98:261-7), antimalarial quinines (Claessen, et al., Trop Med Int Health, (1998) 3:482-9), salicylates (Matz, Ann Otol Rhinol Laryngol Suppl (1990) 148:39-41), and interferon polypeptides (Formann, et al., Am J Gastroenterol (2004) 99:873-77).

SUMMARY OF THE INVENTION

Described herein are pharmaceutically acceptable salts of (4R,7S)-2-(3-(4-chlorophenyl)ureido)-9-methyl-5,6,7,8-tetrahydro-4H-4,7-epiminocyclohepta[b]thiophene-3-carboxamide, including pharmaceutically acceptable solvates (including hydrates), polymorphs, and amorphous phases, and methods of use thereof. Also described are pharmaceutically acceptable aliphatic or aromatic sulfonic acid salts of (4R,7S)-2-(3-(4-chlorophenyl)ureido)-9-methyl-5,6,7,8-tetrahydro-4H-4,7-epiminocyclohepta[b]thiophene-3-carboxamide, including pharmaceutically acceptable solvates (including hydrates), polymorphs, and amorphous phases, and methods of use thereof. Also described are pharmaceutically acceptable methanesulfonic acid, ethanesulfonic acid, benzenesulfonic acid, p-toluenesulfonic acid, or 1,2-ethanedisulfonic acid salts of (4R,7S)-2-(3-(4-chlorophenyl)ureido)-9-methyl-5,6,7,8-tetrahydro-4H-4,7-epiminocyclohepta[b]thiophene-3-carboxamide, including pharmaceutically acceptable solvates (including hydrates), polymorphs, and amorphous phases, and methods of use thereof. Also described is the pharmaceutically acceptable methanesulfonic acid salt of (4R,7S)-2-(3-(4-chlorophenyl)ureido)-9-methyl-5,6,7,8-tetrahydro-4H-4,7-epiminocyclohepta[b]thiophene-3-carboxamide, including pharmaceutically acceptable solvates (including hydrates), polymorphs, and amorphous phases, and methods of use thereof. In some embodiments described herein is a crystalline form of a methanesulfonic acid salt of (4R,7S)-2-(3-(4-chlorophenyl)ureido)-9-methyl-5,6,7,8-tetrahydro-4H-4,7-epiminocyclohepta[b]thiophene-3-carboxamide, and methods of use thereof.

In some embodiments described herein, pharmaceutically acceptable methanesulfonic acid, ethanesulfonic acid, benzenesulfonic acid, p-toluenesulfonic acid, or 1,2-ethanedisulfonic acid salts of (4R,7S)-2-(3-(4-chlorophenyl)ureido)-9-methyl-5,6,7,8-tetrahydro-4H-4,7-epiminocyclohepta[b]thiophene-3-carboxamide, including pharmaceutically acceptable solvates (including hydrates), polymorphs, and amorphous phases are used in the manufacture of medicaments for preventing or treating sensory hair cell death, or for preventing or treating hearing loss, or for protecting against kidney damage in an individual receiving an aminoglycoside antibiotic. In some embodiments, the pharmaceutically acceptable methanesulfonic acid salt of (4R,7S)-2-(3-(4-chlorophenyl)ureido)-9-methyl-5,6,7,8-tetrahydro-4H-4,7-epiminocyclohepta[b]thiophene-3-carboxamide, including pharmaceutically acceptable solvates (including hydrates), polymorphs, and amorphous phases is used in the manufacture of medicaments for preventing or treating sensory hair cell death, or for preventing or treating hearing loss, or for protecting against kidney damage in an individual receiving an aminoglycoside antibiotic.

In one aspect, described herein is a crystalline form of a mesylate salt of (4R,7S)-2-(3-(4-chlorophenyl)ureido)-9-methyl-5,6,7,8-tetrahydro-4H-4,7-epiminocyclohepta[b]thiophene-3-carboxamide, or solvate thereof.

In one embodiment, is a crystalline form of a mesylate salt of (4R,7S)-2-(3-(4-chlorophenyl)ureido)-9-methyl-5,6,7,8-tetrahydro-4H-4,7-epiminocyclohepta[b]thiophene-3-carboxamide, or solvate thereof, wherein the crystalline form has at least one of the following properties:

(a) an X-ray powder diffraction (XRPD) pattern substantially the same as shown in FIG. 1;
(b) an X-ray powder diffraction (XRPD) pattern with characteristic peaks at 7.6° 2-Theta, 10.6° 2-Theta, 15.0° 2-Theta, 16.0° 2-Theta, 16.8° 2-Theta, 17.7° 2-Theta, 21.9° 2-Theta, and 22.5° 2-Theta;
(c) a thermo-gravimetric analysis (TGA) substantially similar to the one set forth in FIG. 2;
(d) an infrared (IR) spectrum substantially similar to the one set forth in FIG. 5;
(e) an infrared (IR) spectrum with peaks at about 1698 cm$^{-1}$, 1537 cm$^{-1}$, 1494 cm$^{-1}$, 1159 cm$^{-1}$, 1039 cm$^{-1}$, 830 cm$^{-1}$, and 784 cm$^{-1}$; or
(f) combinations thereof.

In some embodiments is a crystalline form of a mesylate salt of (4R,7S)-2-(3-(4-chlorophenyl)ureido)-9-methyl-5,6,7,8-tetrahydro-4H-4,7-epiminocyclohepta[b]thiophene-3-carboxamide, or solvate thereof, wherein the crystalline form has an X-ray powder diffraction (XRPD) pattern substantially the same as shown in FIG. 1.

In some embodiments is a crystalline form of a mesylate salt of (4R,7S)-2-(3-(4-chlorophenyl)ureido)-9-methyl-5,6,7,8-tetrahydro-4H-4,7-epiminocyclohepta[b]thiophene-3-carboxamide, or solvate thereof, wherein the crystalline form has an X-ray powder diffraction (XRPD) pattern with characteristic peaks at 7.6° 2-Theta, 10.6° 2-Theta, 15.0° 2-Theta, 16.0° 2-Theta, 16.8° 2-Theta, 17.7° 2-Theta, 21.9° 2-Theta, and 22.5° 2-Theta.

In some embodiments is a crystalline form of a mesylate salt of (4R,7S)-2-(3-(4-chlorophenyl)ureido)-9-methyl-5,6,7,8-tetrahydro-4H-4,7-epiminocyclohepta[b]thiophene-3-carboxamide, or solvate thereof, wherein the crystalline form has a thermo-gravimetric analysis (TGA) substantially similar to the one set forth in FIG. 2.

In some embodiments is a crystalline form of a mesylate salt of (4R,7S)-2-(3-(4-chlorophenyl)ureido)-9-methyl-5,6,7,8-tetrahydro-4H-4,7-epiminocyclohepta[b]thiophene-3-carboxamide, or solvate thereof, wherein the crystalline form has an Infrared (IR) spectrum substantially similar to the one set forth in FIG. 5.

In some embodiments is a crystalline form of a mesylate salt of (4R,7S)-2-(3-(4-chlorophenyl)ureido)-9-methyl-5,6,7,8-tetrahydro-4H-4,7-epiminocyclohepta[b]thiophene-3-carboxamide, or solvate thereof, wherein the crystalline form has an infrared (IR) spectrum with peaks at about 1698 cm$^{-1}$, 1537 cm$^{-1}$, 1494 cm$^{-1}$, 1159 cm$^{-1}$, 1039 cm$^{-1}$, 830 cm$^{-1}$, and 784 cm$^{-1}$.

In some embodiments is a crystalline form of a mesylate salt of (4R,7S)-2-(3-(4-chlorophenyl)ureido)-9-methyl-5,6,7,8-tetrahydro-4H-4,7-epiminocyclohepta[b]thiophene-3-carboxamide, or solvate thereof, wherein the crystalline form is characterized as having properties: (a) an X-ray powder diffraction (XRPD) pattern substantially the same as shown in FIG. 1; (b) an X-ray powder diffraction (XRPD) pattern with characteristic peaks at 7.6° 2-Theta, 10.6° 2-Theta, 15.0° 2-Theta, 16.0° 2-Theta, 16.8° 2-Theta, 17.7° 2-Theta, 21.9° 2-Theta, and 22.5° 2-Theta; (c) a thermogravimetric analysis (TGA) substantially similar to the one set forth in FIG. 2; (d) an Infrared (IR) spectrum substantially similar to the one set forth in FIG. 5; and (e) an infrared (IR) spectrum with peaks at about 1698 cm$^{-1}$, 1537 cm$^{-1}$, 1494 cm$^{-1}$, 1159 cm$^{-1}$, 1039 cm$^{-1}$, 830 cm$^{-1}$, and 784 cm$^{-1}$.

In some embodiments is a crystalline form of a mesylate salt of (4R,7S)-2-(3-(4-chlorophenyl)ureido)-9-methyl-5,6,7,8-tetrahydro-4H-4,7-epiminocyclohepta[b]thiophene-3-carboxamide, or solvate thereof, wherein the crystalline form is obtained from toluene, water, acetonitrile, acetonitrile/water, acetone, acetone/water, tert-butyl methyl ether, 2-butanone, ethyl acetate, isopropyl acetate, tetrahydrofuran, tetrahydrofuran/water, or 2-methyltetrahydrofuran.

In some embodiments is a crystalline form of a mesylate salt of (4R,7S)-2-(3-(4-chlorophenyl)ureido)-9-methyl-5,6,7,8-tetrahydro-4H-4,7-epiminocyclohepta[b]thiophene-3-carboxamide, or solvate thereof, wherein the crystalline form is obtained from acetonitrile, acetonitrile/water, ethyl acetate, or tetrahydrofuran.

In some embodiments is a crystalline form of a mesylate salt of (4R,7S)-2-(3-(4-chlorophenyl)ureido)-9-methyl-5,6,7,8-tetrahydro-4H-4,7-epiminocyclohepta[b]thiophene-3-carboxamide, or solvate thereof, wherein the crystalline form is obtained from acetonitrile.

In some embodiments is a crystalline form of a mesylate salt of (4R,7S)-2-(3-(4-chlorophenyl)ureido)-9-methyl-5,6,7,8-tetrahydro-4H-4,7-epiminocyclohepta[b]thiophene-3-carboxamide, wherein the crystalline form is unsolvated.

In some embodiments is a crystalline form of a mesylate salt of (4R,7S)-2-(3-(4-chlorophenyl)ureido)-9-methyl-5,6,7,8-tetrahydro-4H-4,7-epiminocyclohepta[b]thiophene-3-carboxamide, or solvate thereof, wherein the crystalline form is anhydrous.

In another aspect, described herein is a pharmaceutical composition comprising a crystalline form of a mesylate salt of (4R,7S)-2-(3-(4-chlorophenyl)ureido)-9-methyl-5,6,7,8-tetrahydro-4H-4,7-epiminocyclohepta[b]thiophene-3-carboxamide, or solvate thereof, and at least one inactive ingredient selected from pharmaceutically acceptable carriers, diluents, and excipients.

In another aspect, described herein is a pharmaceutical composition comprising a crystalline form of a mesylate salt of (4R,7S)-2-(3-(4-chlorophenyl)ureido)-9-methyl-5,6,7,8-tetrahydro-4H-4,7-epiminocyclohepta[b]thiophene-3-carboxamide, or solvate thereof, for use in medicine.

In some embodiments is (4R,7S)-2-(3-(4-chlorophenyl)ureido)-9-methyl-5,6,7,8-tetrahydro-4H-4,7-epiminocyclohepta[b]thiophene-3-carboxamide mesylate, or solvate thereof.

In some embodiments is a pharmaceutical composition comprising (4R,7S)-2-(3-(4-chlorophenyl)ureido)-9-methyl-5,6,7,8-tetrahydro-4H-4,7-epiminocyclohepta[b]thiophene-3-carboxamide mesylate, or solvate thereof, and at least one inactive ingredient selected from pharmaceutically acceptable carriers, diluents, and excipients.

In some embodiments is (4R,7S)-2-(3-(4-chlorophenyl)ureido)-9-methyl-5,6,7,8-tetrahydro-4H-4,7-epiminocyclohepta[b]thiophene-3-carboxamide mesylate, or solvate thereof, for use in medicine.

In some embodiments is (4R,7S)-2-(3-(4-chlorophenyl)ureido)-9-methyl-5,6,7,8-tetrahydro-4H-4,7-epiminocyclohepta[b]thiophene-3-carboxamide mesylate, wherein the mesylate is crystalline.

In some embodiments is (4R,7S)-2-(3-(4-chlorophenyl)ureido)-9-methyl-5,6,7,8-tetrahydro-4H-4,7-epiminocyclohepta[b]thiophene-3-carboxamide mesylate, wherein the mesylate is amorphous.

In some embodiments is a pharmaceutical composition comprising a crystalline form of a mesylate salt of (4R,7S)-2-(3-(4-chlorophenyl)ureido)-9-methyl-5,6,7,8-tetrahydro-4H-4,7-epiminocyclohepta[b]thiophene-3-carboxamide, or solvate thereof, and at least one inactive ingredient selected from pharmaceutically acceptable carriers, diluents, and excipients, further comprising an aminoglycoside antibiotic.

In some embodiments is a pharmaceutical composition comprising a crystalline form of a mesylate salt of (4R,7S)-2-(3-(4-chlorophenyl)ureido)-9-methyl-5,6,7,8-tetrahydro-4H-4,7-epiminocyclohepta[b]thiophene-3-carboxamide, or solvate thereof, and at least one inactive ingredient selected from pharmaceutically acceptable carriers, diluents, and excipients, further comprising an aminoglycoside antibiotic selected from streptomycin, neomycin, framycetin, paromomycin, paromomycin sulfate, ribostamycin, kanamycin, amikacin, arbekacin, bekanamycin, dibekacin, tobramycin, spectinomycin, hygromycin B, gentamicin, netilmicin, sisomicin, isepamicin, verdamicin, and astromicin.

In some embodiments is a pharmaceutical composition comprising a crystalline form of a mesylate salt of (4R,7S)-2-(3-(4-chlorophenyl)ureido)-9-methyl-5,6,7,8-tetrahydro-4H-4,7-epiminocyclohepta[b]thiophene-3-carboxamide, or solvate thereof, and at least one inactive ingredient selected from pharmaceutically acceptable carriers, diluents, and excipients, further comprising streptomycin.

In some embodiments is a pharmaceutical composition comprising a crystalline form of a mesylate salt of (4R,7S)-2-(3-(4-chlorophenyl)ureido)-9-methyl-5,6,7,8-tetrahydro-4H-4,7-epiminocyclohepta[b]thiophene-3-carboxamide, or solvate thereof, and at least one inactive ingredient selected from pharmaceutically acceptable carriers, diluents, and excipients, further comprising neomycin.

In some embodiments is a pharmaceutical composition comprising a crystalline form of a mesylate salt of (4R,7S)-2-(3-(4-chlorophenyl)ureido)-9-methyl-5,6,7,8-tetrahydro-4H-4,7-epiminocyclohepta[b]thiophene-3-carboxamide, or solvate thereof, and at least one inactive ingredient selected from pharmaceutically acceptable carriers, diluents, and excipients, further comprising amikacin.

In some embodiments is a pharmaceutical composition comprising a crystalline form of a mesylate salt of (4R,7S)-2-(3-(4-chlorophenyl)ureido)-9-methyl-5,6,7,8-tetrahydro- 4H-4,7-epiminocyclohepta[b]thiophene-3-carboxamide, or solvate thereof, and at least one inactive ingredient selected from pharmaceutically acceptable carriers, diluents, and excipients, further comprising gentamicin.

In some embodiments is a pharmaceutical composition comprising a crystalline form of a mesylate salt of (4R,7S)-2-(3-(4-chlorophenyl)ureido)-9-methyl-5,6,7,8-tetrahydro-4H-4,7-epiminocyclohepta[b]thiophene-3-carboxamide, or solvate thereof, and at least one inactive ingredient selected from pharmaceutically acceptable carriers, diluents, and excipients, further comprising kanamycin.

In some embodiments is a pharmaceutical composition comprising a crystalline form of a mesylate salt of (4R,7S)-2-(3-(4-chlorophenyl)ureido)-9-methyl-5,6,7,8-tetrahydro-4H-4,7-epiminocyclohepta[b]thiophene-3-carboxamide, or solvate thereof, and at least one inactive ingredient selected from pharmaceutically acceptable carriers, diluents, and excipients, further comprising tobramycin.

In some embodiments is a pharmaceutical composition comprising a crystalline form of a mesylate salt of (4R,7S)-2-(3-(4-chlorophenyl)ureido)-9-methyl-5,6,7,8-tetrahydro-4H-4,7-epiminocyclohepta[b]thiophene-3-carboxamide, or solvate thereof, and at least one inactive ingredient selected from pharmaceutically acceptable carriers, diluents, and excipients, formulated for oral, intravenous, intramuscular, or subcutaneous administration. In one embodiment, is a pharmaceutical composition comprising the crystalline form of a mesylate salt of (4R,7S)-2-(3-(4-chlorophenyl)ureido)-9-methyl-5,6,7,8-tetrahydro-4H-4,7-epiminocyclohepta[b]thiophene-3-carboxamide, or solvate thereof, and at least one inactive ingredient selected from pharmaceutically acceptable carriers, diluents, and excipients, further comprising an aminoglycoside antibiotic selected from streptomycin, neomycin, framycetin, paromomycin, paromomycin sulfate, ribostamycin, kanamycin, amikacin, arbekacin, bekanamycin, dibekacin, tobramycin, spectinomycin, hygromycin B, gentamicin, netilmicin, sisomicin, isepamicin, verdamicin, and astromicin, formulated for oral, intravenous, intramuscular, or subcutaneous administration. In one embodiment, is a pharmaceutical composition comprising the crystalline form of a mesylate salt of (4R,7S)-2-(3-(4-chlorophenyl)ureido)-9-methyl-5,6,7,8-tetrahydro-4H-4,7-epiminocyclohepta[b]thiophene-3-carboxamide, or solvate thereof, and at least one inactive ingredient selected from pharmaceutically acceptable carriers, diluents, and excipients, further comprising the aminoglycoside antibiotic streptomycin, formulated for oral, intravenous, intramuscular, or subcutaneous administration. In one embodiment, is a pharmaceutical composition comprising the crystalline form of a mesylate salt of (4R,7S)-2-(3-(4-chlorophenyl)ureido)-9-methyl-5,6,7,8-tetrahydro-4H-4,7-epiminocyclohepta[b]thiophene-3-carboxamide, or solvate thereof, and at least one inactive ingredient selected from pharmaceutically acceptable carriers, diluents, and excipients, further comprising the aminoglycoside antibiotic neomycin, formulated for oral, intravenous, intramuscular, or subcutaneous administration. In one embodiment, is a pharmaceutical composition comprising the crystalline form of a mesylate salt of (4R,7S)-2-(3-(4-chlorophenyl)ureido)-9-methyl-5,6,7,8-tetrahydro-4H-4,7-epiminocyclohepta[b]thiophene-3-carboxamide, or solvate thereof, and at least one inactive ingredient selected from pharmaceutically acceptable carriers, diluents, and excipients, further comprising the aminoglycoside antibiotic framycetin, formulated for oral, intravenous, intramuscular, or subcutaneous administration. In one embodiment, is a pharmaceutical composition comprising the crystalline form of a mesylate salt of (4R,7S)-2-(3-(4-chlorophenyl)ureido)-9-methyl-5,6,7,8-tetrahydro-4H-4,7-epiminocyclohepta[b]thiophene-3-carboxamide, or solvate thereof, and at least one inactive ingredient selected from pharmaceutically acceptable carriers, diluents, and excipients, further comprising the aminoglycoside antibiotic paromomycin, formulated for oral, intravenous, intramuscular, or subcutaneous administration. In one embodiment, is a pharmaceutical composition comprising the crystalline form of a mesylate salt of (4R,7S)-2-(3-(4-chlorophenyl)ureido)-9-methyl-5,6,7,8-tetrahydro-4H-4,7-epiminocyclohepta[b]thiophene-3-carboxamide, or solvate thereof, and at least one inactive ingredient selected from pharmaceutically acceptable carriers, diluents, and excipients, further comprising the aminoglycoside antibiotic paromomycin sulfate, formulated for oral, intravenous, intramuscular, or subcutaneous administration. In one embodiment, is a pharmaceutical composition comprising the crystalline form of a mesylate salt of (4R,7S)-2-(3-(4-chlorophenyl)ureido)-9-methyl-5,6,7,8-tetrahydro-4H-4,7-epiminocyclohepta[b]thiophene-3-carboxamide, or solvate thereof, and at least one inactive ingredient selected from pharmaceutically acceptable carriers, diluents, and excipients, further comprising the aminoglycoside antibiotic ribostamycin, formulated for oral, intravenous, intramuscular, or subcutaneous administration. In one embodiment, is a pharmaceutical composition comprising the crystalline form of a mesylate salt of (4R,7S)-2-(3-(4-chlorophenyl)ureido)-9-methyl-5,6,7,8-tetrahydro-4H-4,7-epiminocyclohepta[b]thiophene-3-carboxamide, or solvate thereof, and at least one inactive ingredient selected from pharmaceutically acceptable carriers, diluents, and excipients, further comprising the aminoglycoside antibiotic kanamycin, formulated for oral, intravenous, intramuscular, or subcutaneous administration. In one embodiment, is a pharmaceutical composition comprising the crystalline form of a mesylate salt of (4R,7S)-2-(3-(4-chlorophenyl)ureido)-9-methyl-5,6,7,8-tetrahydro-4H-4,7-epiminocyclohepta[b]thiophene-3-carboxamide, or solvate thereof, and at least one inactive ingredient selected from pharmaceutically acceptable carriers, diluents, and excipients, further comprising the aminoglycoside antibiotic amikacin, formulated for oral, intravenous, intramuscular, or subcutaneous administration. In one embodiment, is a pharmaceutical composition comprising the crystalline form of a mesylate salt of (4R,7S)-2-(3-(4-chlorophenyl)ureido)-9-methyl-5,6,7,8-tetrahydro-4H-4,7-epiminocyclohepta[b]thiophene-3-carboxamide, or solvate thereof, and at least one inactive ingredient selected from pharmaceutically acceptable carriers, diluents, and excipients, further comprising the aminoglycoside antibiotic arbekacin, formulated for oral, intravenous, intramuscular, or subcutaneous administration. In one embodiment, is a pharmaceutical composition comprising the crystalline form of a mesylate salt of (4R,7S)-2-(3-(4-chlorophenyl)ureido)-9-methyl-5,6,7,8-tetrahydro-4H-4,7-epiminocyclohepta[b]thiophene-3-carboxamide, or solvate thereof, and at least one inactive ingredient selected from pharmaceutically acceptable carriers, diluents, and excipients, further comprising the aminoglycoside antibiotic bekanamycin, formulated for oral, intravenous, intramuscular, or subcutaneous administration. In one embodiment, is a pharmaceutical composition comprising the crystalline form of a mesylate salt of (4R,7S)-2-(3-(4-chlorophenyl)ureido)-9-methyl-5,6,7,8-tetrahydro-4H-4,7-epiminocyclohepta[b]thiophene-3-carboxamide, or solvate thereof, and at least one inactive ingredient selected from pharmaceutically acceptable carriers, diluents, and excipients, further comprising the aminoglycoside antibiotic dibekacin, formulated for oral, intravenous, intramuscular, or subcutaneous administration. In one embodiment, is a pharmaceutical composition comprising the crystalline form of a mesylate salt of (4R,7S)-2-(3-(4-chlorophenyl)ureido)-9-methyl-5,6,7,8-tetrahydro-4H-4,7-epiminocyclohepta[b]thiophene-3-carboxamide, or solvate thereof, and at least one inactive ingredient selected from pharmaceutically acceptable carriers, diluents, and excipients, further comprising the aminoglycoside antibiotic tobramycin, formulated for oral, intravenous, intramuscular, or subcutaneous administration. In one embodiment, is a pharmaceutical composition comprising the crystalline form of a mesylate salt of (4R,7S)-2-(3-(4-chlorophenyl)ureido)-9-methyl-5,6,7,8-tetrahydro-4H-4,7-epiminocyclohepta[b]thiophene-3-carboxamide, or solvate thereof, and at least one inactive ingredient selected from pharmaceutically acceptable carriers, diluents, and excipients, further comprising the aminoglycoside antibiotic spectinomycin, formulated for oral, intravenous, intramuscular, or subcutaneous administration. In one embodiment, is a pharmaceutical composition comprising the crystalline form of a mesylate salt of (4R,7S)-2-(3-(4-chlorophenyl)ureido)-9-methyl-5,6,7,8-tetrahydro-4H-4,7-epiminocyclohepta[b]thiophene-3-carboxamide, or solvate thereof, and at least one inactive ingredient selected from pharmaceutically acceptable carriers, diluents, and excipients, further comprising the aminoglycoside antibiotic hygromycin B, formulated for oral, intravenous, intramuscular, or subcutaneous administration. In one embodiment, is a pharmaceutical composition comprising the crystalline form of a mesylate salt of (4R,7S)-2-(3-(4-chlorophenyl)ureido)-9-methyl-5,6,7,8-tetrahydro-4H-4,7-epiminocyclohepta[b]thiophene-3-carboxamide, or solvate thereof, and at least one inactive ingredient selected from pharmaceutically acceptable carriers, diluents, and excipients, further comprising the aminoglycoside antibiotic gentamicin, formulated for oral, intravenous, intramuscular, or subcutaneous administration. In one embodiment, is a pharmaceutical composition comprising the crystalline form of a mesylate salt of (4R,7S)-2-(3-(4-chlorophenyl)ureido)-9-methyl-5,6,7,8-tetrahydro-4H-4,7-epiminocyclohepta[b]thiophene-3-carboxamide, or solvate thereof, and at least one inactive ingredient selected from pharmaceutically acceptable carriers, diluents, and excipients, further comprising an aminoglycoside antibiotic selected netilmicin, formulated for oral, intravenous, intramuscular, or subcutaneous administration. In one embodiment, is a pharmaceutical composition comprising the crystalline form of a mesylate salt of (4R,7S)-2-(3-(4-chlorophenyl)ureido)-9-methyl-5,6,7,8-tetrahydro-4H-4,7-epiminocyclohepta[b]thiophene-3-carboxamide, or solvate thereof, and at least one inactive ingredient selected from pharmaceutically acceptable carriers, diluents, and excipients, further comprising the aminoglycoside antibiotic sisomicin, formulated for oral, intravenous, intramuscular, or subcutaneous administration. In one embodiment, is a pharmaceutical composition comprising the crystalline form of a mesylate salt of (4R,7S)-2-(3-(4-chlorophenyl)ureido)-9-methyl-5,6,7,8-tetrahydro-4H-4,7-epiminocyclohepta[b]thiophene-3-carboxamide, or solvate thereof, and at least one inactive ingredient selected from pharmaceutically acceptable carriers, diluents, and excipients, further comprising the aminoglycoside antibiotic isepamicin, formulated for oral, intravenous, intramuscular, or subcutaneous administration. In one embodiment, is a pharmaceutical composition comprising the crystalline form of a mesylate salt of (4R,7S)-2-(3-(4-chlorophenyl)ureido)-9-methyl-5,6,7,8-tetrahydro-4H-4,7-epiminocyclohepta[b]thiophene-3-carboxamide, or solvate thereof, and at least one inactive ingredient selected from pharmaceutically acceptable carriers, diluents, and excipients, further comprising the aminoglycoside antibiotic verdamicin, formulated for oral, intravenous, intramuscular, or subcutaneous administration. In one embodiment, is a pharmaceutical composition comprising the crystalline form of a mesylate salt of (4R,7S)-2-(3-(4-chlorophenyl)ureido)-9-methyl-5,6,7,8-tetrahydro-4H-4,7-epiminocyclohepta[b]thiophene-3-carboxamide, or solvate thereof, and at least one inactive ingredient selected from pharmaceutically acceptable carriers, diluents, and excipients, further comprising the aminoglycoside antibiotic astromicin, formulated for oral, intravenous, intramuscular, or subcutaneous administration.

In some embodiments is a method for protecting against kidney damage in an individual receiving an aminoglycoside antibiotic comprising administering to the individual a therapeutically effective amount of a crystalline form of a mesylate salt of (4R,7S)-2-(3-(4-chlorophenyl)ureido)-9-methyl-5,6,7,8-tetrahydro-4H-4,7-epiminocyclohepta[b]thiophene-3-carboxamide, or solvate or hydrate thereof. In some embodiments is a method for protecting against kidney damage in an individual receiving an aminoglycoside antibiotic comprising administering to the individual a therapeutically effective amount of a crystalline form of a mesylate salt of (4R,7S)-2-(3-(4-chlorophenyl)ureido)-9-methyl-5,6,7,8-tetrahydro-4H-4,7-epiminocyclohepta[b]thiophene-3-carboxamide, or solvate or hydrate thereof, and a pharmaceutically acceptable excipient.

In some embodiments is a method for preventing or treating hearing loss in an individual comprising administering to the individual a therapeutically effective amount of a crystalline form of a mesylate salt of (4R,7S)-2-(3-(4-chlorophenyl)ureido)-9-methyl-5,6,7,8-tetrahydro-4H-4,7-epiminocyclohepta[b]thiophene-3-carboxamide, or solvate or hydrate thereof. In some embodiments is a method for preventing or treating hearing loss in an individual comprising administering to the individual a therapeutically effective amount of a crystalline form of a mesylate salt of (4R,7S)-2-(3-(4-chlorophenyl)ureido)-9-methyl-5,6,7,8-tetrahydro-4H-4,7-epiminocyclohepta[b]thiophene-3-carboxamide, or solvate or hydrate thereof, and a pharmaceutically acceptable excipient.

In some embodiments is a method for preventing or treating sensory hair cell death in an individual comprising administering to the individual a therapeutically effective amount of a crystalline form of a mesylate salt of (4R,7S)-2-(3-(4-chlorophenyl)ureido)-9-methyl-5,6,7,8-tetrahydro-4H-4,7-epiminocyclohepta[b]thiophene-3-carboxamide, or solvate or hydrate thereof. In some embodiments is a method for preventing or treating sensory hair cell death in an individual comprising administering to the individual a therapeutically effective amount of a crystalline form of a mesylate salt of (4R,7S)-2-(3-(4-chlorophenyl)ureido)-9-methyl-5,6,7,8-tetrahydro-4H-4,7-epiminocyclohepta[b]thiophene-3-carboxamide, or solvate or hydrate thereof, and a pharmaceutically acceptable excipient.

In some embodiments is a method for preventing or treating hearing loss in an individual comprising administering to the individual a therapeutically effective amount of a crystalline form of a mesylate salt of (4R,7S)-2-(3-(4-chlorophenyl)ureido)-9-methyl-5,6,7,8-tetrahydro-4H-4,7-epiminocyclohepta[b]thiophene-3-carboxamide, or solvate or hydrate thereof, wherein the hearing loss is associated with exposure to an ototoxic agent.

In some embodiments is a method for preventing or treating sensory hair cell death in an individual comprising administering to the individual a therapeutically effective amount of a crystalline form of a mesylate salt of (4R,7S)-2-(3-(4-chlorophenyl)ureido)-9-methyl-5,6,7,8-tetrahydro- 4H-4,7-epiminocyclohepta[b]thiophene-3-carboxamide, or solvate or hydrate thereof, wherein the sensory hair cell death is associated with exposure to an ototoxic agent.

In some embodiments is a method for preventing or treating hearing loss in an individual comprising administering to the individual a therapeutically effective amount of a crystalline form of a mesylate salt of (4R,7S)-2-(3-(4-chlorophenyl)ureido)-9-methyl-5,6,7,8-tetrahydro-4H-4,7-epiminocyclohepta[b]thiophene-3-carboxamide, or solvate or hydrate thereof, wherein the hearing loss is associated with exposure to an ototoxic agent and the ototoxic agent is an aminoglycoside antibiotic, chemotherapeutic agent, loop diuretic, antimalarial sesquiterpene lactone endoperoxide, antimalarial quinine, salicylate, or interferon polypeptide.

In some embodiments is a method for preventing or treating sensory hair cell death in an individual comprising administering to the individual a therapeutically effective amount of a crystalline form of a mesylate salt of (4R,7S)-2-(3-(4-chlorophenyl)ureido)-9-methyl-5,6,7,8-tetrahydro-4H-4,7-epiminocyclohepta[b]thiophene-3-carboxamide, or solvate or hydrate thereof, wherein the hearing loss is associated with exposure to an ototoxic agent and the ototoxic agent is an aminoglycoside antibiotic, chemotherapeutic agent, loop diuretic, antimalarial sesquiterpene lactone endoperoxide, antimalarial quinine, salicylate, or interferon polypeptide.

In some embodiments is a method for preventing or treating hearing loss in an individual comprising administering to the individual a therapeutically effective amount of a crystalline form of a mesylate salt of (4R,7S)-2-(3-(4-chlorophenyl)ureido)-9-methyl-5,6,7,8-tetrahydro-4H-4,7-epiminocyclohepta[b]thiophene-3-carboxamide, or solvate or hydrate thereof, wherein the hearing loss is associated with exposure to an ototoxic agent and the ototoxic agent is an aminoglycoside antibiotic. In some embodiments is a method for preventing or treating sensory hair cell death in an individual comprising administering to the individual a therapeutically effective amount of a crystalline form of a mesylate salt of (4R,7S)-2-(3-(4-chlorophenyl)ureido)-9-methyl-5,6,7,8-tetrahydro-4H-4,7-epiminocyclohepta[b]thiophene-3-carboxamide, or solvate or hydrate thereof, wherein the sensory hair cell death is associated with exposure to an ototoxic agent and the ototoxic agent is an aminoglycoside antibiotic.

In some embodiments is a method for preventing or treating hearing loss in an individual comprising administering to the individual a therapeutically effective amount of a crystalline form of a mesylate salt of (4R,7S)-2-(3-(4-chlorophenyl)ureido)-9-methyl-5,6,7,8-tetrahydro-4H-4,7-epiminocyclohepta[b]thiophene-3-carboxamide, or solvate or hydrate thereof, wherein the hearing loss is associated with exposure to an ototoxic agent, the ototoxic agent is an aminoglycoside antibiotic, and the aminoglycoside antibiotic is selected from streptomycin, neomycin, framycetin, paromomycin, paromomycin sulfate, ribostamycin, kanamycin, amikacin, arbekacin, bekanamycin, dibekacin, tobramycin, spectinomycin, hygromycin B, gentamicin, netilmicin, sisomicin, isepamicin, verdamicin, and astromicin. In some embodiments is a method for preventing or treating sensory hair cell death in an individual comprising administering to the individual a therapeutically effective amount of a crystalline form of a mesylate salt of (4R,7S)-2-(3-(4-chlorophenyl)ureido)-9-methyl-5,6,7,8-tetrahydro-4H-4,7-epiminocyclohepta[b]thiophene-3-carboxamide, or solvate or hydrate thereof, wherein the sensory hair cell death is associated with exposure to an ototoxic agent, the ototoxic agent is an aminoglycoside antibiotic, and the aminoglycoside antibiotic is selected from streptomycin, neomycin, framycetin, paromomycin, paromomycin sulfate, ribostamycin, kanamycin, amikacin, arbekacin, bekanamycin, dibekacin, tobramycin, spectinomycin, hygromycin B, gentamicin, netilmicin, sisomicin, isepamicin, verdamicin, and astromicin.

In some embodiments is a method for preventing or treating hearing loss in an individual comprising administering to the individual a therapeutically effective amount of a crystalline form of a mesylate salt of (4R,7S)-2-(3-(4-chlorophenyl)ureido)-9-methyl-5,6,7,8-tetrahydro-4H-4,7-epiminocyclohepta[b]thiophene-3-carboxamide, or solvate or hydrate thereof, wherein the hearing loss is associated with exposure to an ototoxic agent, the ototoxic agent is an aminoglycoside antibiotic, and the aminoglycoside antibiotic is streptomycin. In some embodiments is a method for preventing or treating sensory hair cell death in an individual comprising administering to the individual a therapeutically effective amount of a crystalline form of a mesylate salt of (4R,7S)-2-(3-(4-chlorophenyl)ureido)-9-methyl-5,6,7,8-tetrahydro-4H-4,7-epiminocyclohepta[b]thiophene-3-carboxamide, or solvate or hydrate thereof, wherein the sensory hair cell death is associated with exposure to an ototoxic agent, the ototoxic agent is an aminoglycoside antibiotic, and the aminoglycoside antibiotic is streptomycin.

In some embodiments is a method for preventing or treating hearing loss in an individual comprising administering to the individual a therapeutically effective amount of a crystalline form of a mesylate salt of (4R,7S)-2-(3-(4-chlorophenyl)ureido)-9-methyl-5,6,7,8-tetrahydro-4H-4,7-epiminocyclohepta[b]thiophene-3-carboxamide, or solvate or hydrate thereof, wherein the hearing loss is associated with exposure to an ototoxic agent, the ototoxic agent is an aminoglycoside antibiotic, and the aminoglycoside antibiotic is neomycin. In some embodiments is a method for preventing or treating sensory hair cell death in an individual comprising administering to the individual a therapeutically effective amount of a crystalline form of a mesylate salt of (4R,7S)-2-(3-(4-chlorophenyl)ureido)-9-methyl-5,6,7,8-tetrahydro-4H-4,7-epiminocyclohepta[b]thiophene-3-carboxamide, or solvate or hydrate thereof, wherein the sensory hair cell death is associated with exposure to an ototoxic agent, the ototoxic agent is an aminoglycoside antibiotic, and the aminoglycoside antibiotic is neomycin.

In some embodiments is a method for preventing or treating hearing loss in an individual comprising administering to the individual a therapeutically effective amount of a crystalline form of a mesylate salt of (4R,7S)-2-(3-(4-chlorophenyl)ureido)-9-methyl-5,6,7,8-tetrahydro-4H-4,7-epiminocyclohepta[b]thiophene-3-carboxamide, or solvate or hydrate thereof, wherein the hearing loss is associated with exposure to an ototoxic agent, the ototoxic agent is an aminoglycoside antibiotic, and the aminoglycoside antibiotic is amikacin. In some embodiments is a method for preventing or treating sensory hair cell death in an individual comprising administering to the individual a therapeutically effective amount of a crystalline form of a mesylate salt of (4R,7S)-2-(3-(4-chlorophenyl)ureido)-9-methyl-5,6,7,8-tetrahydro-4H-4,7-epiminocyclohepta[b]thiophene-3-carboxamide, or solvate or hydrate thereof, wherein the sensory hair cell death is associated with exposure to an ototoxic agent, the ototoxic agent is an aminoglycoside antibiotic, and the aminoglycoside antibiotic is amikacin.

In some embodiments is a method for preventing or treating hearing loss in an individual comprising administering to the individual a therapeutically effective amount of a crystalline form of a mesylate salt of (4R,7S)-2-(3-(4- chlorophenyl)ureido)-9-methyl-5,6,7,8-tetrahydro-4H-4,7-epiminocyclohepta[b]thiophene-3-carboxamide, or solvate or hydrate thereof, wherein the hearing loss is associated with exposure to an ototoxic agent, the ototoxic agent is an aminoglycoside antibiotic, and the aminoglycoside antibiotic is gentamicin. In some embodiments is a method for preventing or treating sensory hair cell death in an individual comprising administering to the individual a therapeutically effective amount of a crystalline form of a mesylate salt of (4R,7S)-2-(3-(4-chlorophenyl)ureido)-9-methyl-5,6,7,8-tetrahydro-4H-4,7-epiminocyclohepta[b]thiophene-3-carboxamide, or solvate or hydrate thereof, wherein the sensory hair cell death is associated with exposure to an ototoxic agent, the ototoxic agent is an aminoglycoside antibiotic, and the aminoglycoside antibiotic is gentamicin.

In some embodiments is a method for preventing or treating hearing loss in an individual comprising administering to the individual a therapeutically effective amount of a crystalline form of a mesylate salt of (4R,7S)-2-(3-(4-chlorophenyl)ureido)-9-methyl-5,6,7,8-tetrahydro-4H-4,7-epiminocyclohepta[b]thiophene-3-carboxamide, or solvate or hydrate thereof, wherein the hearing loss is associated with exposure to an ototoxic agent, the ototoxic agent is an aminoglycoside antibiotic, and the aminoglycoside antibiotic is kanamycin In some embodiments is a method for preventing or treating sensory hair cell death in an individual comprising administering to the individual a therapeutically effective amount of a crystalline form of a mesylate salt of (4R,7S)-2-(3-(4-chlorophenyl)ureido)-9-methyl-5,6,7,8-tetrahydro-4H-4,7-epiminocyclohepta[b]thiophene-3-carboxamide, or solvate or hydrate thereof, wherein the sensory hair cell death is associated with exposure to an ototoxic agent, the ototoxic agent is an aminoglycoside antibiotic, and the aminoglycoside antibiotic is kanamycin.

In some embodiments is a method for preventing or treating hearing loss in an individual comprising administering to the individual a therapeutically effective amount of a crystalline form of a mesylate salt of (4R,7S)-2-(3-(4-chlorophenyl)ureido)-9-methyl-5,6,7,8-tetrahydro-4H-4,7-epiminocyclohepta[b]thiophene-3-carboxamide, or solvate or hydrate thereof, wherein the hearing loss is associated with exposure to an ototoxic agent, the ototoxic agent is an aminoglycoside antibiotic, and the aminoglycoside antibiotic is tobramycin. In some embodiments is a method for preventing or treating sensory hair cell death in an individual comprising administering to the individual a therapeutically effective amount of a crystalline form of a mesylate salt of (4R,7S)-2-(3-(4-chlorophenyl)ureido)-9-methyl-5,6,7,8-tetrahydro-4H-4,7-epiminocyclohepta[b]thiophene-3-carboxamide, or solvate or hydrate thereof, wherein the sensory hair cell death is associated with exposure to an ototoxic agent, the ototoxic agent is an aminoglycoside antibiotic, and the aminoglycoside antibiotic is tobramycin.

In some embodiments is a method for preventing or treating hearing loss in an individual comprising administering to the individual a therapeutically effective amount of a crystalline form of a mesylate salt of (4R,7S)-2-(3-(4-chlorophenyl)ureido)-9-methyl-5,6,7,8-tetrahydro-4H-4,7-epiminocyclohepta[b]thiophene-3-carboxamide, or solvate or hydrate thereof, wherein the hearing loss is associated with exposure to an ototoxic agent, and the ototoxic agent is a chemotherapeutic agent. In some embodiments is a method for preventing or treating sensory hair cell death in an individual comprising administering to the individual a therapeutically effective amount of a crystalline form of a mesylate salt of (4R,7S)-2-(3-(4-chlorophenyl)ureido)-9-methyl-5,6,7,8-tetrahydro-4H-4,7-epiminocyclohepta[b]thiophene-3-carboxamide, or solvate or hydrate thereof, wherein the sensory hair cell death is associated with exposure to an ototoxic agent, and the ototoxic agent is a chemotherapeutic agent.

In some embodiments is a method for preventing or treating hearing loss in an individual comprising administering to the individual a therapeutically effective amount of a crystalline form of a mesylate salt of (4R,7S)-2-(3-(4-chlorophenyl)ureido)-9-methyl-5,6,7,8-tetrahydro-4H-4,7-epiminocyclohepta[b]thiophene-3-carboxamide, or solvate or hydrate thereof, wherein the hearing loss is associated with exposure to an ototoxic agent, the ototoxic agent is a chemotherapeutic agent, and the chemotherapeutic agent is cisplatin. In some embodiments is a method for preventing or treating hearing loss in an individual comprising administering to the individual a therapeutically effective amount of a crystalline form of a mesylate salt of (4R,7S)-2-(3-(4-chlorophenyl)ureido)-9-methyl-5,6,7,8-tetrahydro-4H-4,7-epiminocyclohepta[b]thiophene-3-carboxamide, or solvate or hydrate thereof, wherein the hearing loss is associated with exposure to an ototoxic agent, the ototoxic agent is a chemotherapeutic agent, and the chemotherapeutic agent is carboplatin. In some embodiments is a method for preventing or treating sensory hair cell death in an individual comprising administering to the individual a therapeutically effective amount of a crystalline form of a mesylate salt of (4R,7S)-2-(3-(4-chlorophenyl)ureido)-9-methyl-5,6,7,8-tetrahydro-4H-4,7-epiminocyclohepta[b]thiophene-3-carboxamide, or solvate or hydrate thereof, wherein the sensory hair cell death is associated with exposure to an ototoxic agent, the ototoxic agent is a chemotherapeutic agent, and the chemotherapeutic agent is cisplatin. In some embodiments is a method for preventing or treating sensory hair cell death in an individual comprising administering to the individual a therapeutically effective amount of a crystalline form of a mesylate salt of (4R,7S)-2-(3-(4-chlorophenyl)ureido)-9-methyl-5,6,7,8-tetrahydro-4H-4,7-epiminocyclohepta[b]thiophene-3-carboxamide, or solvate or hydrate thereof, wherein the sensory hair cell death is associated with exposure to an ototoxic agent, the ototoxic agent is a chemotherapeutic agent, and the chemotherapeutic agent is carboplatin.

Other objects, features and advantages of the methods and compositions described herein will become apparent from the following detailed description. It should be understood, however, that the detailed description and the specific examples, while indicating specific embodiments, are given by way of illustration only, since various changes and modifications within the spirit and scope of the present disclosure will become apparent to those skilled in the art from this detailed description. The section headings used herein are for organizational purposes only and are not to be construed as limiting the subject matter described.

INCORPORATION BY REFERENCE

All publications, patents, and patent applications mentioned in this specification are herein incorporated by reference to the extent applicable and relevant and to the same extent as if each individual publication, patent, or patent application was specifically and individually indicated to be incorporated by reference.

DETAILED DESCRIPTION OF THE INVENTION

Figure 1:
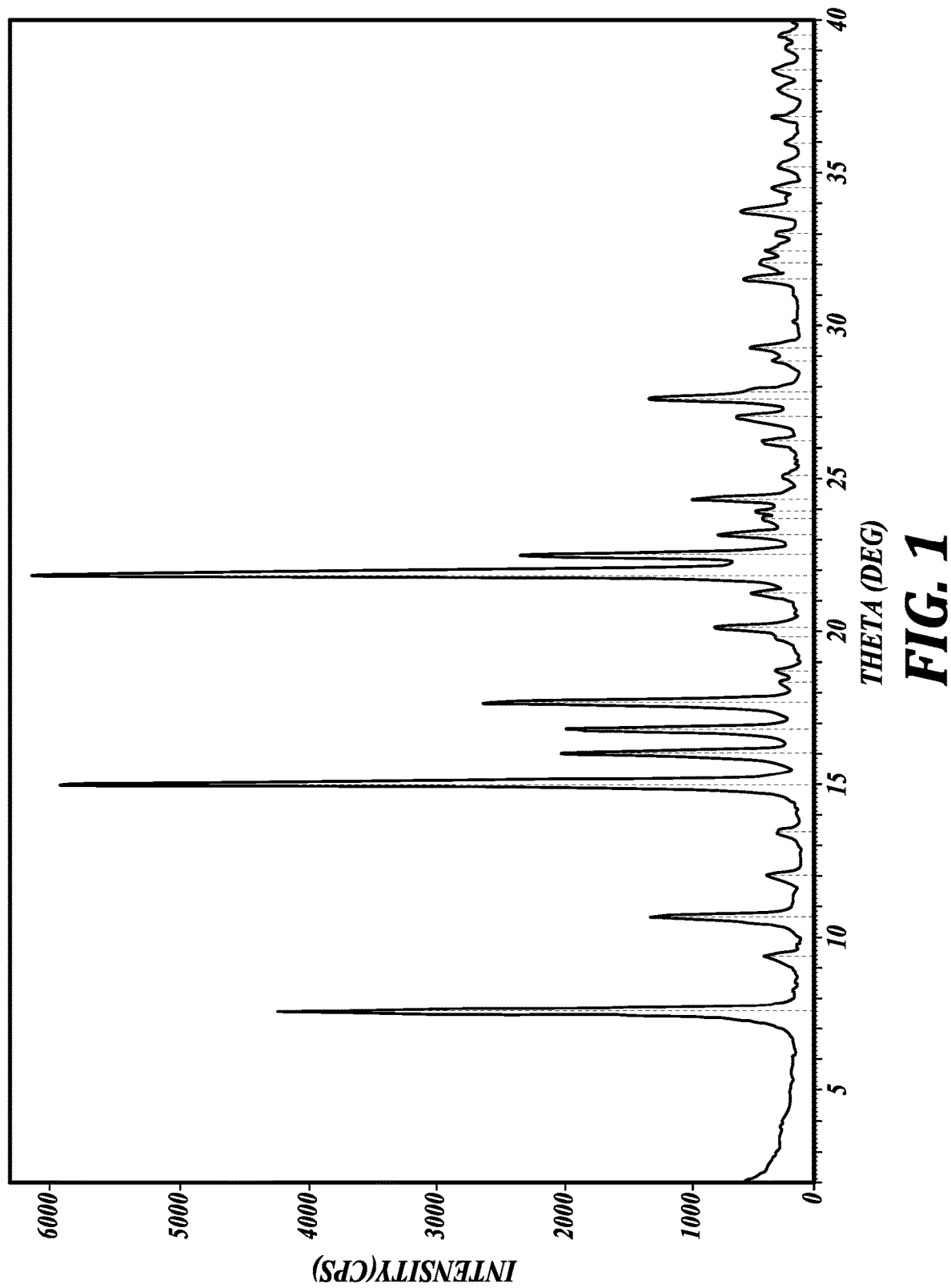
FIG. 1. Illustrates an XRPD spectrum of crystalline (4R,7S)-2-(3-(4-chlorophenyl)ureido)-9-methyl-5,6,7,8-tetrahydro-4H-4,7-epiminocyclohepta[b]thiophene-3-carboxamide mesylate salt.

In some embodiments, the compounds, and compositions comprising these compounds, described herein are useful for preventing or treating sensory hair cell death. In some embodiments, the compounds, and compositions comprising these compounds, described herein are useful for preventing or treating hearing loss. In some embodiments, the compounds, and compositions comprising these compounds, described herein are useful for protecting against kidney damage in an individual receiving an aminoglycoside antibiotic.

Compound B, and Pharmaceutically Acceptable Salts Thereof

In one embodiment is (4R,7S)-2-(3-(4-chlorophenyl)ureido)-9-methyl-5,6,7,8-tetrahydro-4H-4,7-epiminocyclohepta[b]thiophene-3-carboxamide. Compound B is the free base form of (4R,7S)-2-(3-(4-chlorophenyl)ureido)-9-methyl-5,6,7,8-tetrahydro-4H-4,7-epiminocyclohepta[b]thiophene-3-carboxamide. "Compound B" or "(4R,7S)-2-(3-(4-chlorophenyl)ureido)-9-methyl-5,6,7,8-tetrahydro-4H-4,7-epiminocyclohepta[b]thiophene-3-carboxamide" refers to the compound with the following structure:

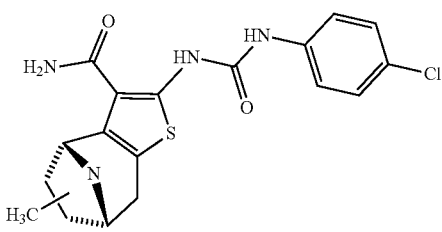

Compound B may alternatively be referred to as: (1R,8S)-4-{[(4-chlorophenyl)carbamoyl]amino}-11-methyl-5-thia-11-azatricyclo[6.2.1.0$^{2,6}$]undeca-2(6),3-diene-3-carboxamide, or (4R,6S)-2-[[[(4-chlorophenyl)amino]carbonyl]amino]-4,5,6,7-tetrahydro-5-methyl-4,6-ethanothieno[3,2-c]pyridine-3-carboxamide.

A wide variety of pharmaceutically acceptable salts are formed from Compound B and include:

acid addition salts formed by reacting Compound B with an organic acid, which include aliphatic mono- and dicarboxylic acids, phenyl-substituted alkanoic acids, hydroxyl alkanoic acids, alkanedioic acids, aromatic acids, aliphatic and aromatic sulfonic acids, amino acids, etc. Aliphatic and aromatic sulfonic acids include, for example, methanesulfonic acid, ethanesulfonic acid, benzenesulfonic acid, p-toluenesulfonic acid, 1,2-ethanedisulfonic acid, and the like;

acid addition salts formed by reacting Compound B with an inorganic acid, which include hydrochloric acid, hydrobromic acid, sulfuric acid, nitric acid, phosphoric acid, hydroiodic acid, hydrofluoric acid, phosphorous acid, and the like.

The term "pharmaceutically acceptable salts" in reference to Compound B refers to a salt of Compound B, which does not cause significant irritation to a mammal to which it is administered and does not substantially abrogate the biological activity and properties of the compound.

It should be understood that a reference to a pharmaceutically acceptable salt includes the solvent addition forms (solvates). Solvates contain either stoichiometric or non-stoichiometric amounts of a solvent, and are formed during the process of product formation or isolation with pharmaceutically acceptable solvents such as water, ethanol, methanol, tert-butyl methyl ether (MTBE), diisopropyl ether (DIPE), ethyl acetate, isopropyl acetate, isopropyl alcohol, methyl isobutyl ketone (MIBK), methyl ethyl ketone (MEK), acetone, nitromethane, tetrahydrofuran (THF), dichloromethane (DCM), dioxane, heptanes, toluene, anisole, acetonitrile, and the like. In one aspect, solvates are formed using, but not limited to, Class 3 solvent(s). In one aspect, solvates are formed using, but not limited to, Class 2 solvent(s). Categories of solvents are defined in, for example, the International Conference on Harmonization of Technical Requirements for Registration of Pharmaceuticals for Human Use (ICH), "Impurities: Guidelines for Residual Solvents Q3C(R6)," (October 2016). Hydrates are formed when the solvent is water, or alcoholates are formed when the solvent is alcohol. In some embodiments, solvates of pharmaceutically acceptable salts of Compound B are conveniently prepared or formed during the processes described herein. In some embodiments, solvates of pharmaceutically acceptable salts of Compound B are anhydrous. In some embodiments, pharmaceutically acceptable salts of Compound B, exist in unsolvated form. In some embodiments, pharmaceutically acceptable salts of Compound B, exist in unsolvated form and are anhydrous.

In one embodiment, the pharmaceutically acceptable salt of Compound B is an aliphatic or aromatic sulfonic acid salt. In one embodiment, the pharmaceutically acceptable salt of Compound B is a methanesulfonate salt (or mesylate salt), ethanesulfonate salt, benzenesulfonate salt (or besylate salt), p-toluenesulfonate salt (or tosylate salt), or 1,2-ethanedisulfonate salt (or edisylate salt). In one embodiment, the pharmaceutically acceptable salt of Compound B is a methanesulfonate salt (or a mesylate salt).

Compound 1

The methanesulfonate salt of Compound B is referred to herein as "Compound 1." Compound 1 is alternatively referred to as "the methanesulfonate," "the mesylate salt," "the mesylate," "(4R,7S)-2-(3-(4-chlorophenyl)ureido)-9-methyl-5,6,7,8-tetrahydro-4H-4,7-epiminocyclohepta[b]thiophene-3-carboxamide mesylate," "(4R,7S)-2-(3-(4-chlorophenyl)ureido)-9-methyl-5,6,7,8-tetrahydro-4H-4,7-epiminocyclohepta[b]thiophene-3-carboxamide mesylate salt," "(4R,7S)-2-(3-(4-chlorophenyl)ureido)-9-methyl-5,6,7,8-tetrahydro-4H-4,7-epiminocyclohepta[b]thiophene-3-carboxamide methanesulfonate salt," or "(4R,7S)-2-(3-(4-chlorophenyl)ureido)-9-methyl-5,6,7,8-tetrahydro-4H-4,7-epiminocyclohepta[b]thiophene-3-carboxamide methanesulfonate."

In other embodiments, Compound 1 is prepared in various forms, including but not limited to, an amorphous phase, crystalline forms, milled forms, and nano-particulate forms.

While not intending to be bound by any particular theory, certain solid forms are characterized by physical properties, e.g., stability, solubility, and dissolution rate, appropriate for pharmaceutical and therapeutic dosage forms. Moreover, while not wishing to be bound by any particular theory, certain solid forms are characterized by physical properties (e.g., density, compressibility, hardness, morphology, cleavage, stickiness, solubility, water uptake, electrical properties, thermal behavior, solid-state reactivity, physical stability, and chemical stability) affecting particular processes (e.g., yield, filtration, washing, drying, milling, mixing, tableting, flowability, dissolution, formulation, and lyophilization) which make certain solid forms suitable for the manufacture of a solid dosage form. Such properties can be determined using particular analytical chemical techniques, including solid-state analytical techniques (e.g., X-ray diffraction, microscopy, spectroscopy and thermal analysis), as described herein and known in the art.

Amorphous Compound 1

In some embodiments, Compound 1 is amorphous. In some embodiments, Compound 1 is amorphous and anhydrous. In some embodiments, amorphous Compound 1 has an X-ray powder diffraction (XRPD) pattern showing a lack of crystallinity.

Crystalline Forms

The identification and selection of a solid form of a pharmaceutical compound are complex, given that a change in solid form may affect a variety of physical and chemical properties, which may provide benefits or drawbacks in processing, formulation, stability, bioavailability, storage, and handling (e.g., shipping), among other important pharmaceutical characteristics. Useful pharmaceutical solids include crystalline solids and amorphous solids, depending on the product and its mode of administration. Amorphous solids are characterized by a lack of long-range structural order, whereas crystalline solids are characterized by structural periodicity. The desired class of pharmaceutical solid depends upon the specific application; amorphous solids are sometimes selected on the basis of, e.g., an enhanced dissolution profile, while crystalline solids may be desirable for properties such as, e.g., physical or chemical stability.

Whether crystalline or amorphous, solid forms of a pharmaceutical compound include single-component and multiple-component solids. Single-component solids consist essentially of the pharmaceutical compound or active ingredient in the absence of other compounds. Variety among single-component crystalline materials may potentially arise from the phenomenon of polymorphism, wherein multiple three-dimensional arrangements exist for a particular pharmaceutical compound.

Notably, it is not possible to predict a priori if crystalline forms of a compound even exist, let alone how to successfully prepare them (see, e.g., Braga and Grepioni, 2005, "Making crystals from crystals: a green route to crystal engineering and polymorphism," *Chem. Commun.*: 3635-3645 (with respect to crystal engineering, if instructions are not very precise and/or if other external factors affect the process, the result can be unpredictable); Jones et al., 2006, Pharmaceutical Cocrystals: An Emerging Approach to Physical Property Enhancement," *MRS Bulletin* 31:875-879 (At present it is not generally possible to computationally predict the number of observable polymorphs of even the simplest molecules); Price, 2004, "The computational prediction of pharmaceutical crystal structures and polymorphism," *Advanced Drug Delivery Reviews* 56:301-319 ("Price"); and Bernstein, 2004, "Crystal Structure Prediction and Polymorphism," *ACA Transactions* 39:14-23 (a great deal still needs to be learned and done before one can state with any degree of confidence the ability to predict a crystal structure, much less polymorphic forms)).

The variety of possible solid forms creates potential diversity in physical and chemical properties for a given pharmaceutical compound. The discovery and selection of solid forms are of great importance in the development of an effective, stable, and marketable pharmaceutical product.

Crystalline Compound 1

Figure 2:
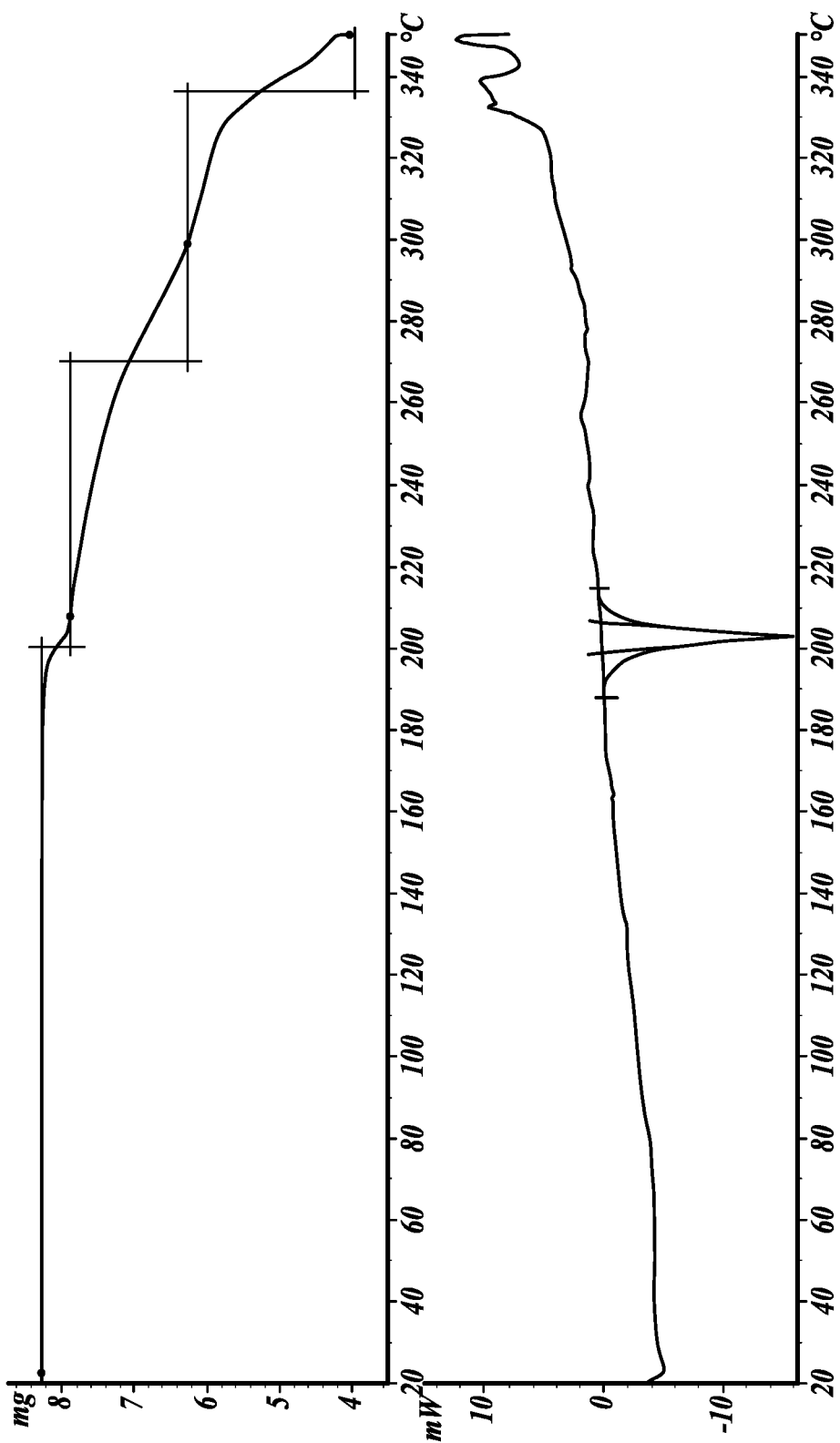
FIG. 2. Illustrates a combined TGA/DSC thermogram of crystalline (4R,7S)-2-(3-(4-chlorophenyl)ureido)-9-methyl-5,6,7,8-tetrahydro-4H-4,7-epiminocyclohepta[b]thiophene-3-carboxamide mesylate salt.
Figure 5:
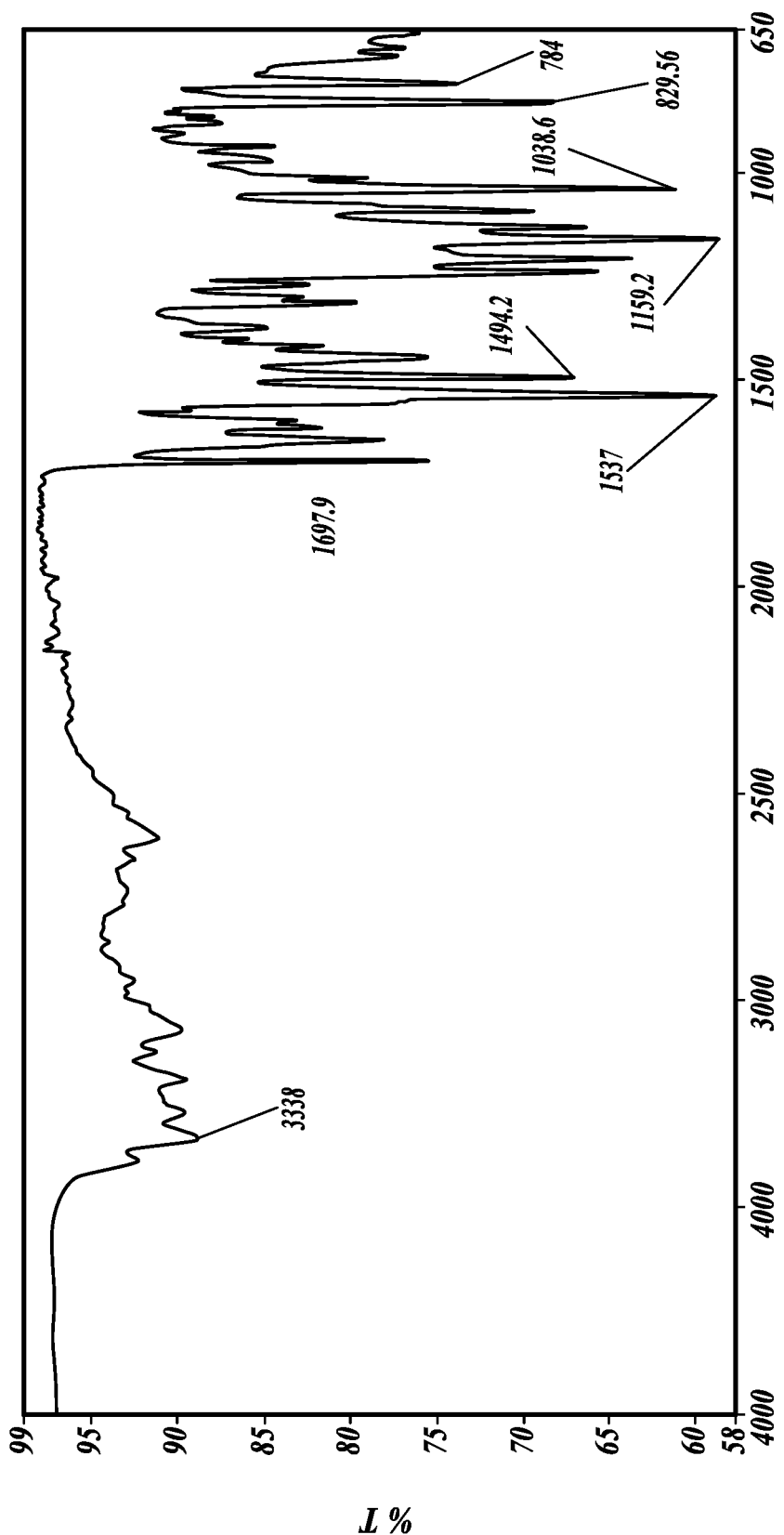
FIG. 5. Illustrates an Infrared (IR) spectrum of crystalline (4R,7S)-2-(3-(4-chlorophenyl)ureido)-9-methyl-5,6,7,8-tetrahydro-4H-4,7-epiminocyclohepta[b]thiophene-3-carboxamide mesylate salt.

In some embodiments, Compound 1 is crystalline. In some embodiments, Compound 1 is crystalline and anhydrous. In some embodiments, crystalline Compound 1 is characterized as having at least one of the following properties:

(a) an X-ray powder diffraction (XRPD) pattern substantially the same as shown in FIG. 1;

(b) an X-ray powder diffraction (XRPD) pattern with characteristic peaks at 7.6° 2-Theta, 10.6° 2-Theta, 15.0° 2-Theta, 16.0° 2-Theta, 16.8° 2-Theta, 17.7° 2-Theta, 21.9° 2-Theta, and 22.5° 2-Theta;

(c) a thermo-gravimetric analysis (TGA) substantially similar to the one set forth in FIG. 2;

(d) an infrared (IR) spectrum substantially similar to the one set forth in FIG. 5;

(e) an infrared (IR) spectrum with peaks at about 1698 $cm^{-1}$, 1537 $cm^{-1}$, 1494 $cm^{-1}$, 1159 $cm^{-1}$, 1039 $cm^{-1}$, 830 $cm^{-1}$, and 784 $cm^{-1}$; or (f) combinations thereof.

In some embodiments, crystalline Compound 1 is characterized as having at least two of the properties selected from (a) to (e). In some embodiments, crystalline Compound 1 is characterized as having at least three of the properties selected from (a) to (e). In some embodiments, crystalline Compound 1 is characterized as having at least four of the properties selected from (a) to (e). In some embodiments, crystalline Compound 1 is characterized as having at least five of the properties selected from (a) to (e). In some embodiments, crystalline Compound 1 is characterized as having at least six of the properties selected from (a) to (e). In some embodiments, crystalline Compound 1 is characterized as having properties (a) to (e).

In some embodiments, crystalline Compound 1 has an X-ray powder diffraction (XRPD) pattern substantially the same as shown in FIG. 1. In some embodiments, crystalline Compound 1 has an X-ray powder diffraction (XRPD) pattern with characteristic peaks at 7.6° 2-Theta, 10.6° 2-Theta, 15.0° 2-Theta, 16.0° 2-Theta, 16.8° 2-Theta, 17.7°

2-Theta, 21.9° 2-Theta, and 22.5° 2-Theta. In some embodiments, crystalline Compound 1 has a thermo-gravimetric analysis (TGA) thermogram substantially similar to the one set forth in FIG. 2. In some embodiments, crystalline Compound 1 has an infrared (IR) spectrum substantially similar to the one set forth in FIG. 5. In some embodiments, crystalline Compound 1 has an infrared (IR) spectrum weak peaks at about 1698 $cm^{-1}$, 1537 $cm^{-1}$, 1494 $cm^{-1}$, 1159 $cm^{-1}$, 1039 $cm^{-1}$, 830 $cm^{-1}$, and 784 $cm^{-1}$. In some embodiments, crystalline Compound 1 is slightly hygroscopic. In some embodiments, crystalline Compound 1 is obtained from toluene, water, acetonitrile, acetonitrile/water, acetone, acetone/water, tert-butyl methyl ether, 2-butanone, ethyl acetate, isopropyl acetate, tetrahydrofuran, tetrahydrofuran/water, or 2-methyltetrahydrofuran. In some embodiments, crystalline Compound 1 is obtained from acetonitrile, acetonitrile/water, ethyl acetate, tetrahydrofuran, or tetrahydrofuran/water. In some embodiments, crystalline Compound 1 is solvated. In some embodiments, crystalline Compound 1 is unsolvated.

Preparation of Crystalline Compound 1

In some embodiments, crystalline forms of Compound 1 are prepared as outlined in the Examples. It is noted that solvents, temperatures and other reaction conditions presented herein may vary.

In certain embodiments, provided herein are methods for making a solid form of Compound 1, comprising 1) obtaining a slurry of Compound B in a solvent; 2) adding a solution of methanesulfonic acid in the same or a different solvent at a temperature; 3) maintaining the resulting mixture at the same or a different temperature for a time; and 4) collecting the resulting solids comprising Compound 1. In certain embodiments, provided herein are methods for making a solid form of Compound 1, comprising 1) obtaining a slurry of Compound B in acetonitrile; 2) adding a solution of methanesulfonic acid in acetonitrile at a temperature; 3) maintaining the resulting mixture at the same or a different temperature for a time; and 4) collecting the resulting solids comprising Compound 1. In certain embodiments, provided herein are methods for making a solid form of Compound 1, comprising 1) obtaining a slurry of Compound B in acetonitrile; 2) adding a solution of methanesulfonic acid in acetonitrile at about 40° C.; 3) maintaining the resulting mixture at about 40° C. for a time; and 4) collecting the resulting solids comprising Compound 1. In certain embodiments, provided herein are methods for making a solid form of Compound 1, comprising 1) obtaining a slurry of Compound B in acetonitrile; 2) adding a solution of methanesulfonic acid in acetonitrile at about 40° C.; 3) maintaining the resulting mixture at about 40° C. for about 3 hours; and 4) collecting the resulting solids comprising Compound 1.

In another embodiment, crystalline Compound 1 is substantially pure. In certain embodiments, the substantially pure crystalline Compound 1 is substantially free of other solid forms, e.g., amorphous solid. In certain embodiments, the purity of the substantially pure crystalline Compound 1 is no less than about 95%, no less than about 96%, no less than about 97%, no less than about 98%, no less than about 98.5%, no less than about 99%, no less than about 99.5%, or no less than about 99.8%.

Suitable Solvents

Therapeutic agents that are administrable to mammals, such as humans, must be prepared by following regulatory guidelines. Such government regulated guidelines are referred to as Good Manufacturing Practice (GMP). GMP guidelines outline acceptable contamination levels of active therapeutic agents, such as, for example, the amount of residual solvent in the final product. In some embodiments, solvents disclosed herein are those that are suitable for use in GMP facilities and consistent with industrial safety concerns. Categories of solvents are defined in, for example, the International Conference on Harmonization of Technical Requirements for Registration of Pharmaceuticals for Human Use (ICH), "Impurities: Guidelines for Residual Solvents Q3C(R6)," (October 2016).

Solvents are categorized into three classes. Class 1 solvents are toxic and are to be avoided. Class 2 solvents are solvents to be limited in use during the manufacture of the therapeutic agent. Class 3 solvents are solvents with low toxic potential and of lower risk to human health. Data for Class 3 solvents indicate that they are less toxic in acute or short-term studies and negative in genotoxicity studies.

Class 1 solvents, which are to be avoided, include: benzene; carbon tetrachloride; 1,2-dichloroethane; 1,1-dichloroethene; and 1,1,1-trichloroethane.

Examples of Class 2 solvents are: acetonitrile, chlorobenzene, chloroform, cumene, cyclohexane, 1,2-dichloroethene, dichloromethane, 1,2-dimethoxyethane, N,N-dimethylacetamide, N,N-dimethylformamide, 1,4-dioxane, 2-ethoxyethanol, ethylene glycol, formamide, hexane, methanol, 2-methoxyethanol, methylbutyl ketone, methylcyclohexane, methylisobutylketone, N-methylpyrrolidone, nitromethane, pyridine, sulfolane, tetrahydrofuran, tetralin, toluene, 1,1,2-trichloroethene and xylene.

Class 3 solvents, which possess low toxicity, include: acetic acid, acetone, anisole, 1-butanol, 2-butanol, butyl acetate, tert-butyl methyl ether (MTBE), dimethyl sulfoxide, ethanol, ethyl acetate, ethyl ether, ethyl formate, formic acid, heptane, isobutyl acetate, isopropyl acetate, methyl acetate, 3-methyl-1-butanol, methylethyl ketone, 2-methyl-1-propanol, pentane, 1-pentanol, 1-propanol, 2-propanol, propyl acetate, and triethylamine.

Residual solvents in active pharmaceutical ingredients (APIs) originate from the manufacture of APIs. In some cases, the solvents are not completely removed by practical manufacturing techniques. Appropriate selection of the solvent for the synthesis of APIs may enhance the yield, or determine characteristics such as crystal form, purity, and solubility. Therefore, the solvent is a critical parameter in the synthetic process.

In some embodiments, compositions comprising Compound 1 comprise an organic solvent(s). In some embodiments, compositions comprising Compound 1 comprise a residual amount of an organic solvent(s). In some embodiments, compositions comprising Compound 1 comprise a residual amount of a Class 3 solvent. In some embodiments, the organic solvent is a Class 3 solvent. In some embodiments, the Class 3 solvent is selected from the group consisting of acetic acid, acetone, anisole, 1-butanol, 2-butanol, butyl acetate, tert-butyl methyl ether (MTBE), dimethyl sulfoxide, ethanol, ethyl acetate, ethyl ether, ethyl formate, formic acid, heptane, isobutyl acetate, isopropyl acetate, methyl acetate, 3-methyl-1-butanol, methylethyl ketone, 2-methyl-1-propanol, pentane, 1-pentanol, 1-propanol, 2-propanol, propyl acetate, and triethylamine. In some embodiments, the Class 3 solvent is selected from the group consisting of acetone, ethyl acetate, isopropyl acetate, tert-butyl methyl ether, heptane, isopropanol, and ethanol.

In some embodiments, compositions comprising Compound 1 comprise a residual amount of a Class 2 solvent. In some embodiments, the organic solvent is a Class 2 solvent. In some embodiments, the Class 2 solvent is selected from the group consisting of acetonitrile, chlorobenzene, chloroform, cumene, cyclohexane, 1,2-dichloroethene, dichloromethane, 1,2-dimethoxyethane, N,N-dimethylacetamide, N,N-dimethylformamide, 1,4-dioxane, 2-ethoxyethanol, ethylene glycol, formamide, hexane, methanol, 2-methoxyethanol, methylbutyl ketone, methylcyclohexane, methylisobutylketone, N-methylpyrrolidone, nitromethane, pyridine, sulfolane, tetrahydrofuran, tetralin, toluene, 1,1,2-trichloroethene and xylene. In some embodiments, the Class 2 solvent is selected from the group consisting of acetonitrile, tetrahydrofuran, and toluene. In some embodiments, the Class 2 solvent is acetonitrile.

In some embodiments, compositions comprising Compound 1 comprise a residual amount of a solvent for which no adequate toxicological data were found. In some embodiments, the organic solvent is a solvent for which no adequate toxicological data were found. In some embodiments, the solvent is selected from the group consisting of 2-butanone and 2-methyltetrahydrofuran.

Certain Terminology

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting. The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features. The term "about" when referring to a number or a numerical range means that the number or numerical range referred to is an approximation within experimental variability (or within statistical experimental error), and thus the number or numerical range may vary between 1% and 15% of the stated number or numerical range.

The section headings used herein are for organizational purposes only and are not to be construed as limiting the subject matter described. All documents, or portions of documents, cited in the application including, but not limited to, patents, patent applications, articles, books, manuals, and treatises are hereby expressly incorporated by reference in their entirety.

The term "acceptable" or "pharmaceutically acceptable", with respect to a formulation, composition or ingredient, as used herein, means having no persistent detrimental effect on the general health of the subject being treated or does not abrogate the biological activity or properties of the compound, and is relatively nontoxic.

As used herein, "amelioration" of the symptoms of a particular disease, disorder, or condition by administration of a particular compound or pharmaceutical composition refers to any lessening of severity, delay in onset, slowing of progression, or shortening of duration, whether permanent or temporary, lasting or transient that can be attributed to or associated with administration of the compound or composition.

"Bioavailability" refers to the percentage of Compound 1 dosed that is delivered into the general circulation of the animal or human being studied. The total exposure ($AUC_{(0-\infty)}$) of a drug when administered intravenously is usually defined as 100% bioavailable (F %). "Oral bioavailability" refers to the extent to which Compound 1 is absorbed into the general circulation when the pharmaceutical composition is taken orally as compared to intravenous injection.

"Blood plasma concentration" refers to the concentration of Compound 1 in the plasma component of blood of a subject. It is understood that the plasma concentration of Compound 1 may vary significantly between subjects, due to variability with respect to metabolism and/or possible interactions with other therapeutic agents. In accordance with one embodiment disclosed herein, the blood plasma concentration of Compound 1 may vary from subject to subject. Likewise, values such as maximum plasma concentration ($C_{max}$) or time to reach maximum plasma concentration ($T_{max}$), or total area under the plasma concentration time curve ($AUC_{(0-\infty)}$) may vary from subject to subject. Due to this variability, the amount necessary to constitute "a therapeutically effective amount" of Compound 1 may vary from subject to subject.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition including a compound as disclosed herein required to provide a clinically significant decrease in disease symptoms without undue adverse side effects. An appropriate "effective amount" in any individual case may be determined using techniques, such as a dose escalation study. The term "therapeutically effective amount" includes, for example, a prophylactically effective amount. An "effective amount" of a compound disclosed herein is an amount effective to achieve a desired pharmacologic effect or therapeutic improvement without undue adverse side effects. It is understood that "an effect amount" or "a therapeutically effective amount" can vary from subject to subject, due to variation in metabolism of Compound 1, age, weight, general condition of the subject, the condition being treated, the severity of the condition being treated, and the judgment of the prescribing physician. By way of example only, therapeutically effective amounts may be determined by a dose escalation clinical trial.

The terms "enhance" or "enhancing" means to increase or prolong either in potency or duration a desired effect. By way of example, "enhancing" the effect of therapeutic agents refers to the ability to increase or prolong, either in potency or duration, the effect of therapeutic agents on during treatment of a disease, disorder, or condition. An "enhancing-effective amount," as used herein, refers to an amount adequate to enhance the effect of a therapeutic agent in the treatment of a disease, disorder, or condition. When used in a patient, amounts effective for this use will depend on the severity and course of the disease, disorder, or condition, previous therapy, the patient's health status and response to the drugs, and the judgment of the treating physician.

The term "prophylactically effective amount," as used herein, refers that amount of a composition applied to a patient which will relieve to some extent one or more of the symptoms of a disease, condition or disorder being treated. In such prophylactic applications, such amounts may depend on the patient's state of health, weight, and the like. As an example, one can determine such prophylactically effective amounts by a dose escalation clinical trial.

The term "subject" as used herein, refers to an animal which is the object of treatment, observation or experiment. By way of example only, a subject may be, but is not limited to, a mammal including, but not limited to, a human.

As used herein, the term "target activity" refers to a biological activity capable of being modulated by a selective modulator. Certain exemplary target activities include, but are not limited to, binding affinity, signal transduction, enzymatic activity, tumor growth, inflammation or inflammation-related processes, and amelioration of one or more symptoms associated with a disease or condition.

The terms "treat," "treating" or "treatment", as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition. The terms "treat," "treating" or "treatment", include, but are not limited to, prophylactic and/or therapeutic treatments.

As used herein, $EC_{50}$ refers to a dosage, concentration or amount of a particular test compound that elicits a dose-dependent response at 50% of maximal expression of a particular response that is induced, provoked or potentiated by the particular test compound.

Pharmaceutical Compositions/Formulations

Pharmaceutical compositions may be formulated in a conventional manner using one or more physiologically acceptable carriers including excipients and auxiliaries which facilitate processing of the active compounds into preparations which can be used pharmaceutically. Proper formulation is dependent upon the route of administration chosen. A summary of pharmaceutical compositions described herein may be found, for example, in *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery* Systems, Seventh Ed. (Lippincott Williams & Wilkins 1999), herein incorporated by reference in their entirety.

A pharmaceutical composition, as used herein, refers to a mixture of Compound 1 with other chemical components, such as carriers, stabilizers, diluents, dispersing agents, suspending agents, thickening agents, and/or excipients. The pharmaceutical composition facilitates administration of the compound to a mammal. In practicing the methods of treatment or use provided herein, therapeutically effective amounts of Compound 1 are administered in a pharmaceutical composition to a mammal having a disease, disorder, or condition to be treated. Preferably, the mammal is a human. A therapeutically effective amount can vary widely depending on the severity of the disease, the age and relative health of the subject, the potency of the compound used and other factors. The compounds can be used singly or in combination with one or more therapeutic agents as components of mixtures.

The term "pharmaceutical combination" as used herein, means a product that results from the mixing or combining of more than one active ingredient and includes both fixed and non-fixed combinations of the active ingredients. The term "fixed combination" means that the active ingredients, e.g. Compound 1, and a co-agent, are both administered to a patient simultaneously in the form of a single entity or dosage. The term "non-fixed combination" means that the active ingredients, e.g. Compound 1, and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

In some embodiments, crystalline Compound 1 is incorporated into pharmaceutical compositions to provide solid oral dosage forms. In other embodiments, crystalline Compound 1 is used to prepare pharmaceutical compositions other than oral solid dosage forms. The pharmaceutical formulations described herein can be administered to a subject by multiple administration routes, including but not limited to, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

Pharmaceutical compositions including a compound described herein may be manufactured in a conventional manner, such as, by way of example only, by means of conventional mixing, dissolving, granulating, dragee-making, levigating, emulsifying, encapsulating, entrapping or compression processes.

Dosage Forms

The pharmaceutical compositions described herein can be formulated for administration to a mammal via any conventional means including, but not limited to, oral, parenteral (e.g., intravenous, subcutaneous, or intramuscular), buccal, intranasal, rectal, or transdermal administration routes. As used herein, the term "subject" is used to mean an animal, preferably a mammal, including a human or non-human. The terms patient and subject may be used interchangeably.

Moreover, the pharmaceutical compositions described herein, which include Compound 1 can be formulated into any suitable dosage form, including but not limited to, solid oral dosage forms, controlled release formulations, fast melt formulations, effervescent formulations, tablets, powders, pills, capsules, delayed release formulations, extended release formulations, pulsatile release formulations, multiparticulate formulations, and mixed immediate release and controlled release formulations.

Pharmaceutical preparations for oral use can be obtained by mixing one or more solid excipients with one or more of the compounds described herein, optionally grinding the resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents may be added, such as the cross-linked croscarmellose sodium, polyvinylpyrrolidone, agar, or alginic acid or a salt thereof such as sodium alginate.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

In some embodiments, the solid dosage forms disclosed herein may be in the form of a tablet, (including a suspension tablet, a fast-melt tablet, a bite-disintegration tablet, a rapid-disintegration tablet, an effervescent tablet, or a caplet), a pill, a powder (including a sterile packaged powder, a dispensable powder, or an effervescent powder) a capsule (including both soft or hard capsules, e.g., capsules made from animal-derived gelatin or plant-derived HPMC, or "sprinkle capsules"), solid dispersion, solid solution, bio-erodible dosage form, controlled release formulations, pulsatile release dosage forms, multiparticulate dosage forms, pellets, granules, or an aerosol. In other embodiments, the pharmaceutical formulation is in the form of a powder. In still other embodiments, the pharmaceutical formulation is in the form of a tablet, including but not limited to, a fast-melt tablet. Additionally, pharmaceutical formulations described herein may be administered as a single capsule or in multiple capsule dosage form. In some embodiments, the pharmaceutical formulation is administered in two, or three, or four, capsules or tablets.

In some embodiments, solid dosage forms, e.g., tablets, effervescent tablets, and capsules, are prepared by mixing particles of Compound 1 with one or more pharmaceutical excipients to form a bulk blend composition. When referring to these bulk blend compositions as homogeneous, it is meant that the particles of Compound 1 are dispersed evenly throughout the composition so that the composition may be readily subdivided into equally effective unit dosage forms, such as tablets, pills, and capsules. The individual unit dosages may also include film coatings, which disintegrate upon oral ingestion or upon contact with diluent. These formulations can be manufactured by conventional pharmacological techniques.

Conventional pharmacological techniques include, e.g., one or a combination of methods: (1) dry mixing, (2) direct compression, (3) milling, (4) dry or non-aqueous granulation, (5) wet granulation, or (6) fusion. See, e.g., Lachman et al., *The Theory and Practice of Industrial Pharmacy* (1986). Other methods include, e.g., spray drying, pan coating, melt granulation, granulation, fluidized bed spray drying or coating (e.g., wurster coating), tangential coating, top spraying, tableting, extruding and the like.

The pharmaceutical solid dosage forms described herein can include Compound 1, and one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof. In still other aspects, using standard coating procedures, such as those described in *Remington's Pharmaceutical Sciences*, 20th Edition (2000), a film coating is provided around the formulation of Compound 1. In one embodiment, some or all of the particles of the Compound 1 are coated. In another embodiment, some or all of the particles of the Compound 1 are microencapsulated. In still another embodiment, the particles of the Compound 1 are not microencapsulated and are uncoated.

Suitable carriers for use in the solid dosage forms described herein include, but are not limited to, acacia, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassium phosphate, sodium stearoyl lactylate, carrageenan, monoglyceride, diglyceride, pregelatinized starch, hydroxypropylmethylcellulose, hydroxypropylmethylcellulose acetate stearate, sucrose, microcrystalline cellulose, lactose, mannitol, and the like.

Suitable filling agents for use in the solid dosage forms described herein include, but are not limited to, lactose, calcium carbonate, calcium phosphate, dibasic calcium phosphate, calcium sulfate, microcrystalline cellulose, cellulose powder, dextrose, dextrates, dextran, starches, pregelatinized starch, hydroxypropylmethycellulose (HPMC), hydroxypropylmethycellulose phthalate, hydroxypropylmethylcellulose acetate stearate (HPMCAS), sucrose, xylitol, lactitol, mannitol, sorbitol, sodium chloride, polyethylene glycol, and the like.

In order to release the Compound 1 from a solid dosage form matrix as efficiently as possible, disintegrants are often used in the formulation, especially when the dosage forms are compressed with binder. Disintegrants help rupturing the dosage form matrix by swelling or capillary action when moisture is absorbed into the dosage form. Suitable disintegrants for use in the solid dosage forms described herein include, but are not limited to, natural starch such as corn starch or potato starch, a pregelatinized starch such as National 1551 or Amijel®, or sodium starch glycolate such as Promogel® or Explotab®, a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crospovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like. In some embodiments provided herein, the disintegrating agent is selected from the group consisting of natural starch, a pregelatinized starch, a sodium starch, methylcrystalline cellulose, methylcellulose, croscarmellose, croscarmellose sodium, cross-linked sodium carboxymethylcellulose, cross-linked carboxymethylcellulose, cross-linked croscarmellose, cross-linked starch such as sodium starch glycolate, cross-linked polymer such as crospovidone, cross-linked polyvinylpyrrolidone, sodium alginate, a clay, or a gum. In some embodiments provided herein, the disintegrating agent is croscarmellose sodium.

Binders impart cohesiveness to solid oral dosage form formulations: for powder filled capsule formulation, they aid in plug formation that can be filled into soft or hard shell capsules and for tablet formulation, they ensure the tablet remaining intact after compression and help assure blend uniformity prior to a compression or fill step. Materials suitable for use as binders in the solid dosage forms described herein include, but are not limited to, carboxymethylcellulose, methylcellulose (e.g., Methocel®), hydroxypropylmethylcellulose (e.g. Hypromellose USP Pharmacoat-603, hydroxypropylmethylcellulose acetate stearate (Aqoate HS-LF and HS), hydroxyethylcellulose, hydroxypropylcellulose (e.g., Klucel®), ethylcellulose (e.g., Ethocel®), and microcrystalline cellulose (e.g., Avicel®), microcrystalline dextrose, amylose, magnesium aluminum silicate, polysaccharide acids, bentonites, gelatin, polyvinylpyrrolidone/vinyl acetate copolymer, crospovidone, povidone, starch, pregelatinized starch, tragacanth, dextrin, a sugar, such as sucrose (e.g., Dipac®), glucose, dextrose, molasses, mannitol, sorbitol, xylitol (e.g., Xylitab®), lactose, a natural or synthetic gum such as acacia, tragacanth, ghatti gum, mucilage of isapol husks, starch, polyvinylpyrrolidone (e.g., Povidone® CL, Kollidon® CL, Polyplasdone® XL-10, and Povidone® K-12), larch arabogalactan, Veegum®, polyethylene glycol, waxes, sodium alginate, and the like.

In general, binder levels of 20-70% are used in powder-filled gelatin capsule formulations. Binder usage level in tablet formulations varies whether direct compression, wet granulation, roller compaction, or usage of other excipients such as fillers which itself can act as moderate binder. Formulators skilled in art can determine the binder level for the formulations, but binder usage level of up to 70% in tablet formulations is common.

Suitable lubricants or glidants for use in the solid dosage forms described herein include, but are not limited to, stearic acid, calcium hydroxide, talc, corn starch, sodium stearyl fumarate, alkali-metal and alkaline earth metal salts, such as calcium, magnesium, stearic acid, sodium stearates, magnesium stearate, zinc stearate, waxes, Stearowet®, boric acid, sodium benzoate, sodium acetate, sodium chloride, leucine, a polyethylene glycol or a methoxypolyethylene glycol such as Carbowax™, PEG 4000, PEG 5000, PEG 6000, propylene glycol, sodium oleate, glyceryl behenate, glyceryl palmitostearate, glyceryl benzoate, magnesium or sodium lauryl sulfate, and the like. In some embodiments provided herein, the lubricant is selected from the group consisting of stearic acid, calcium hydroxide, talc, corn starch, sodium stearyl fumarate, stearic acid, sodium stearates, magnesium stearate, zinc stearate, and waxes. In some embodiments provided herein, the lubricant is magnesium stearate.

Suitable diluents for use in the solid dosage forms described herein include, but are not limited to, sugars (including lactose, sucrose, and dextrose), polysaccharides (including dextrates and maltodextrin), polyols (including mannitol, xylitol, and sorbitol), cyclodextrins and the like. In some embodiments provided herein, the diluent is selected from the group consisting of lactose, sucrose, dextrose, dextrates, maltodextrin, mannitol, xylitol, sorbitol, cyclodextrins, calcium phosphate, calcium sulfate, starches, modified starches, microcrystalline cellulose, microcellulose, and talc. In some embodiments provided herein, the diluent is microcrystalline cellulose.

The term "non water-soluble diluent" represents compounds typically used in the formulation of pharmaceuticals, such as calcium phosphate, calcium sulfate, starches, modified starches, microcrystalline cellulose, microcellulose (e.g., having a density of about 0.45 g/cm$^3$, e.g. Avicel, powdered cellulose), and talc.

Suitable wetting agents for use in the solid dosage forms described herein include, for example, oleic acid, glyceryl monostearate, sorbitan monooleate, sorbitan monolaurate, triethanolamine oleate, polyoxyethylene sorbitan monooleate, polyoxyethylene sorbitan monolaurate, quaternary ammonium compounds (e.g., Polyquat 10®), sodium oleate, sodium lauryl sulfate, magnesium stearate, sodium docusate, triacetin, vitamin E TPGS, and the like.

Suitable surfactants for use in the solid dosage forms described herein include, for example, sodium lauryl sulfate, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like. In some embodiments provided herein, the surfactant is selected from the group consisting of sodium lauryl sulfate, sorbitan monooleate, polyoxyethylene sorbitan monooleate, polysorbates, polaxomers, bile salts, glyceryl monostearate, copolymers of ethylene oxide and propylene oxide. In some embodiments provided herein, the surfactant is sodium lauryl sulfate.

Suitable suspending agents for use in the solid dosage forms described here include, but are not limited to, polyvinylpyrrolidone, e.g., polyvinylpyrrolidone K12, polyvinylpyrrolidone K17, polyvinylpyrrolidone K25, or polyvinylpyrrolidone K30, polyethylene glycol, e.g., the polyethylene glycol can have a molecular weight of about 300 to about 6000, or about 3350 to about 4000, or about 7000 to about 5400, vinyl pyrrolidone/vinyl acetate copolymer (S630), sodium carboxymethylcellulose, methylcellulose, hydroxy-propylmethylcellulose, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone, and the like.

Suitable antioxidants for use in the solid dosage forms described herein include, for example, e.g., butylated hydroxytoluene (BHT), sodium ascorbate, and tocopherol.

It should be appreciated that there is considerable overlap between additives used in the solid dosage forms described herein. Thus, the above-listed additives should be taken as merely exemplary, and not limiting, of the types of additives that can be included in solid dosage forms described herein. The amounts of such additives can be readily determined by one skilled in the art, according to the particular properties desired.

In other embodiments, one or more layers of the pharmaceutical formulation are plasticized. Illustratively, a plasticizer is generally a high boiling point solid or liquid. Suitable plasticizers can be added from about 0.01% to about 50% by weight (w/w) of the coating composition. Plasticizers include, but are not limited to, diethyl phthalate, citrate esters, polyethylene glycol, glycerol, acetylated glycerides, triacetin, polypropylene glycol, polyethylene glycol, triethyl citrate, dibutyl sebacate, stearic acid, stearol, stearate, and castor oil.

Compressed tablets are solid dosage forms prepared by compacting the bulk blend of the formulations described above. In various embodiments, compressed tablets which are designed to dissolve in the mouth will include one or more flavoring agents. In other embodiments, the compressed tablets will include a film surrounding the final compressed tablet. In some embodiments, the film coating can provide a delayed release of Compound 1 from the formulation. In other embodiments, the film coating aids in patient compliance (e.g., Opadry® coatings or sugar coating). Film coatings including Opadry® typically range from about 1% to about 3% of the tablet weight. In other embodiments, the compressed tablets include one or more excipients.

A capsule may be prepared, for example, by placing the bulk blend of the formulation of Compound 1 inside of a capsule. In some embodiments, the formulations (non-aqueous suspensions and solutions) are placed in a soft gelatin capsule. In some embodiments, the formulations (non-aqueous suspensions and solutions) are placed in a hard shell gelatin capsule. In other embodiments, the formulations are placed in standard gelatin capsules or non-gelatin capsules such as capsules comprising HPMC. In other embodiments, the formulation is placed in a sprinkle capsule, wherein the capsule may be swallowed whole or the capsule may be opened and the contents sprinkled on food prior to eating. In some embodiments, the therapeutic dose is split into multiple (e.g., two, three, or four) capsules. In some embodiments, the entire dose of the formulation is delivered in a capsule form.

In various embodiments, the particles of Compound 1 and one or more excipients are dry blended and compressed into a mass, such as a tablet, having a hardness sufficient to provide a pharmaceutical composition that substantially disintegrates within less than about 30 minutes, less than about 35 minutes, less than about 40 minutes, less than about 45 minutes, less than about 50 minutes, less than about 55 minutes, or less than about 60 minutes, after oral administration, thereby releasing the formulation into the gastrointestinal fluid.

In another aspect, dosage forms may include microencapsulated formulations. In some embodiments, one or more other compatible materials are present in the microencapsulation material. Exemplary materials include, but are not limited to, pH modifiers, erosion facilitators, anti-foaming agents, antioxidants, flavoring agents, and carrier materials such as binders, suspending agents, disintegration agents, filling agents, surfactants, solubilizers, stabilizers, lubricants, wetting agents, and diluents.

Materials useful for the microencapsulation described herein include materials compatible with Compound 1 which sufficiently isolate the Compound 1 from other non-compatible excipients. Materials compatible with Compound 1 are those that delay the release of the compounds of Compound 1 in vivo.

Exemplary microencapsulation materials useful for delaying the release of the formulations including compounds described herein, include, but are not limited to, hydroxypropyl cellulose ethers (HPC) such as Klucel® or Nisso HPC, low-substituted hydroxypropyl cellulose ethers (L-HPC), hydroxypropyl methyl cellulose ethers (HPMC) such as Seppifilm-LC, Pharmacoat®, Metolose SR, Methocel®-E, Opadry YS, PrimaFlo, Benecel MP824, and Benecel MP843, methylcellulose polymers such as Methocel®-A, hydroxypropylmethylcellulose acetate stearate Aqoat (HF-LS, HF-LG, HF-MS) and Metolose®, Ethylcelluloses (EC) and mixtures thereof such as E461, Ethocel®, Aqualon®-EC, Surelease®, Polyvinyl alcohol (PVA) such as Opadry AMB, hydroxyethylcelluloses such as Natrosol®, carboxymethylcelluloses and salts of carboxymethylcelluloses (CMC) such as Aqualon®-CMC, polyvinyl alcohol and polyethylene glycol co-polymers such as Kollicoat IR®, monoglycerides (Myverol), triglycerides (KLX), polyethylene glycols, modified food starch, acrylic polymers and mixtures of acrylic polymers with cellulose ethers such as Eudragit® EPO, Eudragit® L30D-55, Eudragit® FS 30D Eudragit® L100-55, Eudragit® L100, Eudragit® S100, Eudragit® RD100, Eudragit® E100, Eudragit® L12.5, Eudragit® S12.5, Eudragit® NE30D, and Eudragit® NE 40D, cellulose acetate phthalate, sepifilms such as mixtures of HPMC and stearic acid, cyclodextrins, and mixtures of these materials.

In still other embodiments, plasticizers such as polyethylene glycols, e.g., PEG 300, PEG 400, PEG 600, PEG 1450, PEG 3350, and PEG 800, stearic acid, propylene glycol, oleic acid, and triacetin are incorporated into the microencapsulation material. In other embodiments, the microencapsulating material useful for delaying the release of the pharmaceutical compositions is from the USP or the National Formulary (NF). In yet other embodiments, the microencapsulation material is Klucel. In still other embodiments, the microencapsulation material is methocel.

Microencapsulated Compound 1 may be formulated by several methods, illustrative examples of which include, e.g., spray drying processes, spinning disk-solvent processes, hot melt processes, spray chilling methods, fluidized bed, electrostatic deposition, centrifugal extrusion, rotational suspension separation, polymerization at liquid-gas or solid-gas interface, pressure extrusion, or spraying solvent extraction bath. In addition to these, several chemical techniques, e.g., complex coacervation, solvent evaporation, polymer-polymer incompatibility, interfacial polymerization in liquid media, in situ polymerization, in-liquid drying, and desolvation in liquid media could also be used. Furthermore, other methods such as roller compaction, extrusion/spheronization, coacervation, or nanoparticle coating may also be used.

In one embodiment, the particles of Compound 1 are microencapsulated prior to being formulated into one of the above forms. In still another embodiment, some or most of the particles are coated prior to being further formulated by using standard coating procedures, such as those described in *Remington's Pharmaceutical Sciences,* 20th Edition (2000).

In other embodiments, the solid dosage formulations of the Compound 1 are plasticized (coated) with one or more layers. Illustratively, a plasticizer is generally a high boiling point solid or liquid. Suitable plasticizers can be added from about 0.01% to about 50% by weight (w/w) of the coating composition. Plasticizers include, but are not limited to, diethyl phthalate, citrate esters, polyethylene glycol, glycerol, acetylated glycerides, triacetin, polypropylene glycol, polyethylene glycol, triethyl citrate, dibutyl sebacate, stearic acid, stearol, stearate, and castor oil.

In other embodiments, a powder including the formulations with Compound 1 may be formulated to include one or more pharmaceutical excipients and flavors. Such a powder may be prepared, for example, by mixing the formulation and optional pharmaceutical excipients to form a bulk blend composition. Additional embodiments also include a suspending agent and/or a wetting agent. This bulk blend is uniformly subdivided into unit dosage packaging or multi-dosage packaging units.

In still other embodiments, effervescent powders are also prepared in accordance with the present disclosure. Effervescent salts have been used to disperse medicines in water for oral administration. Effervescent salts are granules or coarse powders containing a medicinal agent in a dry mixture, usually composed of sodium bicarbonate, citric acid and/or tartaric acid. When salts of the compositions described herein are added to water, the acids and the base react to liberate carbon dioxide gas, thereby causing "effervescence." Examples of effervescent salts include, e.g., the following ingredients: sodium bicarbonate or a mixture of sodium bicarbonate and sodium carbonate, citric acid and/or tartaric acid. Any acid-base combination that results in the liberation of carbon dioxide can be used in place of the combination of sodium bicarbonate and citric and tartaric acids, as long as the ingredients were suitable for pharmaceutical use and result in a pH of about 6.0 or higher.

In some embodiments, the solid dosage forms described herein can be formulated as enteric coated delayed release oral dosage forms, i.e., as an oral dosage form of a pharmaceutical composition as described herein which utilizes an enteric coating to affect release in the small intestine of the gastrointestinal tract. The enteric coated dosage form may be a compressed or molded or extruded tablet/mold (coated or uncoated) containing granules, powder, pellets, beads or particles of the active ingredient and/or other composition components, which are themselves coated or uncoated. The enteric coated oral dosage form may also be a capsule (coated or uncoated) containing pellets, beads or granules of the solid carrier or the composition, which are themselves coated or uncoated.

The term "delayed release" as used herein refers to the delivery so that the release can be accomplished at some generally predictable location in the intestinal tract more distal to that which would have been accomplished if there had been no delayed release alterations. In some embodiments the method for delay of release is coating. Any coatings should be applied to a sufficient thickness such that the entire coating does not dissolve in the gastrointestinal fluids at pH below about 5, but does dissolve at pH about 5 and above. It is expected that any anionic polymer exhibiting a pH-dependent solubility profile can be used as an enteric coating in the methods and compositions described herein to achieve delivery to the lower gastrointestinal tract. In some embodiments the polymers described herein are anionic carboxylic polymers. In other embodiments, the polymers and compatible mixtures thereof, and some of their properties, include, but are not limited to:

Shellac, also called purified lac, a refined product obtained from the resinous secretion of an insect. This coating dissolves in media of pH>7;

Acrylic polymers. The performance of acrylic polymers (primarily their solubility in biological fluids) can vary based on the degree and type of substitution. Examples of suitable acrylic polymers include methacrylic acid copolymers and ammonium methacrylate copolymers. The Eudragit series E, L, S, RL, RS and NE (Rohm Pharma) are available as solubilized in organic solvent, aqueous dispersion, or dry powders. The Eudragit series RL, NE, and RS are insoluble in the gastrointestinal tract but are permeable and are used primarily for colonic targeting. The Eudragit series E dissolve in the stomach. The Eudragit series L, L-30D and S are insoluble in the stomach and dissolve in the intestine;

Cellulose Derivatives. Examples of suitable cellulose derivatives are ethyl cellulose; and reaction mixtures of partial acetate esters of cellulose with phthalic anhydride. The performance can vary based on the degree and type of substitution. Cellulose acetate phthalate (CAP) dissolves in pH>6. Aquateric (FMC) is an aqueous based system and is a spray dried CAP psuedolatex with particles <1 µm. Other components in Aquateric can include pluronics, Tweens, and acetylated monoglycerides. Other suitable cellulose derivatives include: cellulose acetate trimellitate (Eastman); methylcellulose (Pharmacoat, Methocel); hydroxypropylmethyl cellulose phthalate (HPMCP); hydroxypropylmethyl cellulose succinate (HPMCS); and hydroxypropylmethylcellulose acetate succinate (e.g., AQOAT (Shin Etsu)). The performance can vary based on the degree and type of substitution. For example, HPMCP such as, HP-50, HP-55, HP-55S, or HP-55F grades are suitable. The performance can vary based on the degree and type of substitution. For example, suitable grades of hydroxypropylmethylcellulose acetate succinate include, but are not limited to, AS-LG (LF), which dissolves at pH 5, AS-MG (MF), which dissolves at pH 5.5, and AS-HG (HF), which dissolves at higher pH. These polymers are offered as granules, or as fine powders for aqueous dispersions; Poly Vinyl Acetate Phthalate (PVAP). PVAP dissolves in pH>5, and it is much less permeable to water vapor and gastric fluids.

In some embodiments, the coating can, and usually does, contain a plasticizer and possibly other coating excipients such as colorants, talc, and/or magnesium stearate. Suitable plasticizers include triethyl citrate (Citroflex 2), triacetin (glyceryl triacetate), acetyl triethyl citrate (Citroflec A2), Carbowax 400 (polyethylene glycol 400), diethyl phthalate, tributyl citrate, acetylated monoglycerides, glycerol, fatty acid esters, propylene glycol, and dibutyl phthalate. In particular, anionic carboxylic acrylic polymers usually will contain 10-25% by weight of a plasticizer, especially dibutyl phthalate, polyethylene glycol, triethyl citrate and triacetin. Conventional coating techniques such as spray or pan coating are employed to apply coatings. The coating thickness must be sufficient to ensure that the oral dosage form remains intact until the desired site of topical delivery in the intestinal tract is reached.

Colorants, detackifiers, surfactants, antifoaming agents, lubricants (e.g., carnuba wax or PEG) may be added to the coatings besides plasticizers to solubilize or disperse the coating material, and to improve coating performance and the coated product.

In other embodiments, the formulations described herein, which include Compound 1 are delivered using a pulsatile dosage form. A pulsatile dosage form is capable of providing one or more immediate release pulses at predetermined time points after a controlled lag time or at specific sites. Other types of controlled release systems may be used. Examples of such delivery systems include, e.g., polymer-based systems, such as polylactic and polyglycolic acid, polyanhydrides and polycaprolactone; porous matrices, nonpolymer-based systems that are lipids, including sterols, such as cholesterol, cholesterol esters and fatty acids, or neutral fats, such as mono-, di- and triglycerides; hydrogel release systems; silastic systems; peptide-based systems; wax coatings, bioerodible dosage forms, compressed tablets using conventional binders and the like. See, e.g., Liberman et al., *Pharmaceutical Dosage Forms,* 2 Ed., Vol. 1, pp. 209-214 (1990); Singh et al., *Encyclopedia of Pharmaceutical Technology,* $2^{nd}$ Ed., pp. 751-753 (2002); U.S. Pat. Nos. 4,327,725, 4,624,848, 4,968,509, 5,461,140, 5,456,923, 5,516,527, 5,622,721, 5,686,105, 5,700,410, 5,977,175, 6,465,014 and 6,932,983, each of which is specifically incorporated by reference.

In some embodiments, pharmaceutical formulations are provided that include particles of Compound 1 and at least one dispersing agent or suspending agent for oral administration to a subject. The formulations may be a powder and/or granules for suspension and, upon admixture with water, a substantially uniform suspension is obtained.

It is to be appreciated that there is overlap between the above-listed additives used in the aqueous dispersions or suspensions described herein, since a given additive is often classified differently by different practitioners in the field, or is commonly used for any of several different functions. Thus, the above-listed additives should be taken as merely exemplary, and not limiting, of the types of additives that can be included in formulations described herein. The amounts of such additives can be readily determined by one skilled in the art, according to the particular properties desired.

Methods

In some embodiments is a method for protecting against kidney damage in an individual receiving an aminoglycoside antibiotic comprising administering to the individual a therapeutically effective amount of a crystalline form of Compound 1 described herein. In some embodiments is a method for protecting against kidney damage in an individual receiving an aminoglycoside antibiotic comprising administering to the individual a therapeutically effective amount of a crystalline form of Compound 1 described herein wherein the aminoglycoside antibiotic is selected from streptomycin, neomycin, framycetin, paromomycin, paromomycin sulfate, ribostamycin, kanamycin, amikacin, arbekacin, bekanamycin, dibekacin, tobramycin, spectinomycin, hygromycin B, gentamicin, netilmicin, sisomicin, isepamicin, verdamicin, and astromicin.

In some embodiments disclosed herein is a method for preventing or treating hearing loss in an individual comprising administering to the individual a therapeutically effective amount of a crystalline form of Compound 1 described herein. In some embodiments disclosed herein is a method for preventing hearing loss in an individual comprising administering to the individual a therapeutically effective amount of a crystalline form of Compound 1 described herein. In some embodiments disclosed herein is a method for preventing hearing loss in an individual comprising administering to the individual a therapeutically effective amount of a crystalline form of Compound 1 described herein, wherein the hearing loss is associated with exposure to an ototoxic agent. In some embodiments disclosed herein is a method for preventing hearing loss in an individual comprising administering to the individual a therapeutically effective amount of a crystalline form of Compound 1 described herein, wherein the hearing loss is associated with exposure to an ototoxic agent selected from an aminoglycoside antibiotic, chemotherapeutic agent, loop diuretic, antimalarial sesquiterpene lactone endoperoxide, antimalarial quinine, salicylate, or interferon polypeptide. In some embodiments disclosed herein is a method for preventing hearing loss in an individual comprising administering to the individual a therapeutically effective amount of a crystalline form of Compound 1 described herein, wherein the hearing loss is associated with exposure to an aminoglycoside antibiotic. In some embodiments disclosed herein is a method for preventing hearing loss in an individual comprising administering to the individual a therapeutically effective amount of a crystalline form of Compound 1 described herein, wherein the hearing loss is associated with exposure to an aminoglycoside antibiotic selected from streptomycin, neomycin, framycetin, paromomycin, paromomycin sulfate, ribostamycin, kanamycin, amikacin, arbekacin, bekanamycin, dibekacin, tobramycin, spectinomycin, hygromycin B, gentamicin, netilmicin, sisomicin, isepamicin, verdamicin, and astromicin. In some embodiments disclosed herein is a method for preventing hearing loss in an individual comprising administering to the individual a therapeutically effective amount of a crystalline form of Compound 1 described herein, wherein the hearing loss is associated with exposure to a chemotherapeutic agent. In some embodiments disclosed herein is a method for preventing hearing loss in an individual comprising administering to the individual a therapeutically effective amount of a crystalline form of Compound 1 described herein, wherein the hearing loss is associated with exposure to a chemotherapeutic agent selected from cisplatin or carboplatin. In some embodiments disclosed herein is a method for preventing hearing loss in an individual comprising administering to the individual a therapeutically effective amount of a crystalline form of Compound 1 described herein, wherein the hearing loss is associated with exposure to cisplatin. In some embodiments disclosed herein is a method for preventing hearing loss in an individual comprising administering to the individual a therapeutically effective amount of a crystalline form of Compound 1 described herein, wherein the hearing loss is associated with exposure to carboplatin. In some embodiments disclosed herein is a method for preventing hearing loss in an individual comprising administering to the individual a therapeutically effective amount of a crystalline form of Compound 1 described herein, wherein the hearing loss is associated with exposure to a loop diuretic. In some embodiments disclosed herein is a method for preventing hearing loss in an individual comprising administering to the individual a therapeutically effective amount of a crystalline form of Compound 1 described herein, wherein the hearing loss is associated with exposure to an antimalarial sesquiterpene lactone endoperoxide. In some embodiments disclosed herein is a method for preventing hearing loss in an individual comprising administering to the individual a therapeutically effective amount of a crystalline form of Compound 1 described herein, wherein the hearing loss is associated with exposure to an antimalarial quinine. In some embodiments disclosed herein is a method for preventing hearing loss in an individual comprising administering to the individual a therapeutically effective amount of a crystalline form of Compound 1 described herein, wherein the hearing loss is associated with exposure to a salicylate. In some embodiments disclosed herein is a method for preventing hearing loss in an individual comprising administering to the individual a therapeutically effective amount of a crystalline form of Compound 1 described herein, wherein the hearing loss is associated with exposure to an interferon polypeptide. In some embodiments disclosed herein is a method for treating hearing loss in an individual comprising administering to the individual a therapeutically effective amount of a crystalline form of Compound 1 described herein. In some embodiments disclosed herein is a method for treating hearing loss in an individual comprising administering to the individual a therapeutically effective amount of a crystalline form of Compound 1 described herein, wherein the hearing loss is associated with exposure to an ototoxic agent. In some embodiments disclosed herein is a method for treating hearing loss in an individual comprising administering to the individual a therapeutically effective amount of a crystalline form of Compound 1 described herein, wherein the hearing loss is associated with exposure to an ototoxic agent selected from an aminoglycoside antibiotic, chemotherapeutic agent, loop diuretic, antimalarial sesquiterpene lactone endoperoxide, antimalarial quinine, salicylate, or interferon polypeptide. In some embodiments disclosed herein is a method for treating hearing loss in an individual comprising administering to the individual a therapeutically effective amount of a crystalline form of Compound 1 described herein, wherein the hearing loss is associated with exposure to an aminoglycoside antibiotic. In some embodiments disclosed herein is a method for treating hearing loss in an individual comprising administering to the individual a therapeutically effective amount of a crystalline form of Compound 1 described herein, wherein the hearing loss is associated with exposure to an aminoglycoside antibiotic selected from streptomycin, neomycin, framycetin, paromomycin, paromomycin sulfate, ribostamycin, kanamycin, amikacin, arbekacin, bekanamycin, dibekacin, tobramycin, spectinomycin, hygromycin B, gentamicin, netilmicin, sisomicin, isepamicin, verdamicin, and astromicin. In some embodiments disclosed herein is a method for treating hearing loss in an individual comprising administering to the individual a therapeutically effective amount of a crystalline form of Compound 1 described herein, wherein the hearing loss is associated with exposure to a chemotherapeutic agent. In some embodiments disclosed herein is a method for treating hearing loss in an individual comprising administering to the individual a therapeutically effective amount of a crystalline form of Compound 1 described herein, wherein the hearing loss is associated with exposure to a chemotherapeutic agent selected from cisplatin or carboplatin. In some embodiments disclosed herein is a method for treating hearing loss in an individual comprising administering to the individual a therapeutically effective amount of a crystalline form of Compound 1 described herein, wherein the hearing loss is associated with exposure to cisplatin. In some embodiments disclosed herein is a method for treating hearing loss in an individual comprising administering to the individual a therapeutically effective amount of a crystalline form of Compound 1 described herein, wherein the hearing loss is associated with exposure to carboplatin. In some embodiments disclosed herein is a method for treating hearing loss in an individual comprising administering to the individual a therapeutically effective amount of a crystalline form of Compound 1 described herein, wherein the hearing loss is associated with exposure to a loop diuretic. In some embodiments disclosed herein is a method for treating hearing loss in an individual comprising administering to the individual a therapeutically effective amount of a crystalline form of Compound 1 described herein, wherein the hearing loss is associated with exposure to an antimalarial sesquiterpene lactone endoperoxide. In some embodiments disclosed herein is a method for treating hearing loss in an individual comprising administering to the individual a therapeutically effective amount of a crystalline form of Compound 1 described herein, wherein the hearing loss is associated with exposure to an antimalarial quinine. In some embodiments disclosed herein is a method for treating hearing loss in an individual comprising administering to the individual a therapeutically effective amount of a crystalline form of Compound 1 described herein, wherein the hearing loss is associated with exposure to a salicylate. In some embodiments disclosed herein is a method for treating hearing loss in an individual comprising administering to the individual a therapeutically effective amount of a crystalline form of Compound 1 described herein, wherein the hearing loss is associated with exposure to an interferon polypeptide.

In some embodiments disclosed herein is a method for preventing or treating sensory hair cell death in an individual comprising administering to the individual a therapeutically effective amount of a crystalline form of Compound 1 described herein. In some embodiments disclosed herein is a method for preventing sensory hair cell death in an individual comprising administering to the individual a therapeutically effective amount of a crystalline form of Compound 1 described herein. In some embodiments disclosed herein is a method for preventing sensory hair cell death in an individual comprising administering to the individual a therapeutically effective amount of a crystalline form of Compound 1 described herein, wherein the sensory hair cell death is associated with exposure to an ototoxic agent. In some embodiments disclosed herein is a method for preventing sensory hair cell death in an individual comprising administering to the individual a therapeutically effective amount of a crystalline form of Compound 1 described herein, wherein the sensory hair cell death is associated with exposure to an ototoxic agent selected from an aminoglycoside antibiotic, chemotherapeutic agent, loop diuretic, antimalarial sesquiterpene lactone endoperoxide, antimalarial quinine, salicylate, or interferon polypeptide. In some embodiments disclosed herein is a method for preventing sensory hair cell death in an individual comprising administering to the individual a therapeutically effective amount of a crystalline form of Compound 1 described herein, wherein the sensory hair cell death is associated with exposure to an aminoglycoside antibiotic. In some embodiments disclosed herein is a method for preventing sensory hair cell death in an individual comprising administering to the individual a therapeutically effective amount of a crystalline form of Compound 1 described herein, wherein the hearing loss is associated with exposure to an aminoglycoside antibiotic selected from streptomycin, neomycin, framycetin, paromomycin, paromomycin sulfate, ribostamycin, kanamycin, amikacin, arbekacin, bekanamycin, dibekacin, tobramycin, spectinomycin, hygromycin B, gentamicin, netilmicin, sisomicin, isepamicin, verdamicin, and astromicin. In some embodiments disclosed herein is a method for preventing sensory hair cell death in an individual comprising administering to the individual a therapeutically effective amount of a crystalline form of Compound 1 described herein, wherein the sensory hair cell death is associated with exposure to a chemotherapeutic agent. In some embodiments disclosed herein is a method for preventing sensory hair cell death in an individual comprising administering to the individual a therapeutically effective amount of a crystalline form of Compound 1 described herein, wherein the sensory hair cell death is associated with exposure to a chemotherapeutic agent selected from cisplatin or carboplatin. In some embodiments disclosed herein is a method for preventing sensory hair cell death in an individual comprising administering to the individual a therapeutically effective amount of a crystalline form of Compound 1 described herein, wherein the sensory hair cell death is associated with exposure to cisplatin. In some embodiments disclosed herein is a method for preventing sensory hair cell death in an individual comprising administering to the individual a therapeutically effective amount of a crystalline form of Compound 1 described herein, wherein the sensory hair cell death is associated with exposure to carboplatin. In some embodiments disclosed herein is a method for preventing sensory hair cell death in an individual comprising administering to the individual a therapeutically effective amount of a crystalline form of Compound 1 described herein, wherein the sensory hair cell death is associated with exposure to a loop diuretic. In some embodiments disclosed herein is a method for preventing sensory hair cell death in an individual comprising administering to the individual a therapeutically effective amount of a crystalline form of Compound 1 described herein, wherein the sensory hair cell death is associated with exposure to an antimalarial sesquiterpene lactone endoperoxide. In some embodiments disclosed herein is a method for preventing sensory hair cell death in an individual comprising administering to the individual a therapeutically effective amount of a crystalline form of Compound 1 described herein, wherein the sensory hair cell death is associated with exposure to an antimalarial quinine. In some embodiments disclosed herein is a method for preventing sensory hair cell death in an individual comprising administering to the individual a therapeutically effective amount of a crystalline form of Compound 1 described herein, wherein the sensory hair cell death is associated with exposure to a salicylate. In some embodiments disclosed herein is a method for preventing sensory hair cell death in an individual comprising administering to the individual a therapeutically effective amount of a crystalline form of Compound 1 described herein, wherein the sensory hair cell death is associated with exposure to an interferon polypeptide. In some embodiments disclosed herein is a method for treating sensory hair cell death in an individual comprising administering to the individual a therapeutically effective amount of a crystalline form of Compound 1 described herein. In some embodiments disclosed herein is a method for treating sensory hair cell death in an individual comprising administering to the individual a therapeutically effective amount of a crystalline form of Compound 1 described herein, wherein the sensory hair cell death is associated with exposure to an ototoxic agent. In some embodiments disclosed herein is a method for treating sensory hair cell death in an individual comprising administering to the individual a therapeutically effective amount of a crystalline form of Compound 1 described herein, wherein the sensory hair cell death is associated with exposure to an ototoxic agent selected from an aminoglycoside antibiotic, chemotherapeutic agent, loop diuretic, antimalarial sesquiterpene lactone endoperoxide, antimalarial quinine, salicylate, or interferon polypeptide. In some embodiments disclosed herein is a method for treating sensory hair cell death in an individual comprising administering to the individual a therapeutically effective amount of a crystalline form of Compound 1 described herein, wherein the sensory hair cell death is associated with exposure to an aminoglycoside antibiotic. In some embodiments disclosed herein is a method for treating sensory hair cell death in an individual comprising administering to the individual a therapeutically effective amount of a crystalline form of Compound 1 described herein, wherein the hearing loss is associated with exposure to an aminoglycoside antibiotic selected from streptomycin, neomycin, framycetin, paromomycin, paromomycin sulfate, ribostamycin, kanamycin, amikacin, arbekacin, bekanamycin, dibekacin, tobramycin, spectinomycin, hygromycin B, gentamicin, netilmicin, sisomicin, isepamicin, verdamicin, and astromicin. In some embodiments disclosed herein is a method for treating sensory hair cell death in an individual comprising administering to the individual a therapeutically effective amount of a crystalline form of Compound 1 described herein, wherein the sensory hair cell death is associated with exposure to a chemotherapeutic agent. In some embodiments disclosed herein is a method for treating sensory hair cell death in an individual comprising administering to the individual a therapeutically effective amount of a crystalline form of Compound 1 described herein, wherein the sensory hair cell death is associated with exposure to a chemotherapeutic agent selected from cisplatin or carboplatin. In some embodiments disclosed herein is a method for treating sensory hair cell death in an individual comprising administering to the individual a therapeutically effective amount of a crystalline form of Compound 1 described herein, wherein the sensory hair cell death is associated with exposure to cisplatin. In some embodiments disclosed herein is a method for treating sensory hair cell death in an individual comprising administering to the individual a therapeutically effective amount of a crystalline form of Compound 1 described herein, wherein the sensory hair cell death is associated with exposure to carboplatin. In some embodiments disclosed herein is a method for treating sensory hair cell death in an individual comprising administering to the individual a therapeutically effective amount of a crystalline form of Compound 1 described herein, wherein the sensory hair cell death is associated with exposure to a loop diuretic. In some embodiments disclosed herein is a method for treating sensory hair cell death in an individual comprising administering to the individual a therapeutically effective amount of a crystalline form of Compound 1 described herein, wherein the sensory hair cell death is associated with exposure to an antimalarial sesquiterpene lactone endoperoxide. In some embodiments disclosed herein is a method for treating sensory hair cell death in an individual comprising administering to the individual a therapeutically effective amount of a crystalline form of Compound 1 described herein, wherein the sensory hair cell death is associated with exposure to an antimalarial quinine. In some embodiments disclosed herein is a method for treating sensory hair cell death in an individual comprising administering to the individual a therapeutically effective amount of a crystalline form of Compound 1 described herein, wherein the sensory hair cell death is associated with exposure to a salicylate. In some embodiments disclosed herein is a method for treating sensory hair cell death in an individual comprising administering to the individual a therapeutically effective amount of a crystalline form of Compound 1 described herein, wherein the hearing loss is associated with exposure to an interferon polypeptide.

Methods of Dosing and Treatment Regimens

The compositions described herein can be administered for prophylactic and/or therapeutic treatments. In therapeutic applications, the compositions are administered to a patient already suffering from a disease or condition, in an amount sufficient to cure or at least partially arrest the symptoms of the disease or condition. Amounts effective for this use will depend on the severity and course of the disease or condition, previous therapy, the patient's health status, weight, and response to the drugs, and the judgment of the treating physician.

In prophylactic applications, compositions containing the compounds described herein are administered to a patient susceptible to or otherwise at risk of a particular disease, disorder, or condition. Such an amount is defined to be a "prophylactically effective amount or dose." In this use, the precise amounts also depend on the patient's state of health, weight, and the like. When used in a patient, effective amounts for this use will depend on the severity and course of the disease, disorder, or condition, previous therapy, the patient's health status and response to the drugs, and the judgment of the treating physician.

In the case wherein the patient's condition does not improve, upon the doctor's discretion the administration of the compounds may be administered chronically, that is, for an extended period of time, including throughout the duration of the patient's life in order to ameliorate or otherwise control or limit the symptoms of the patient's disease or condition.

Once improvement of the patient's conditions has occurred, a maintenance dose is administered, if necessary. Subsequently, the dosage or the frequency of administration, or both, can be reduced, as a function of the symptoms, to a level at which the improved disease, disorder, or condition is retained. Patients can, however, require intermittent treatment on a long-term basis upon any recurrence of symptoms.

The amount of a given agent that will correspond to such an amount will vary depending upon factors such as the particular compound, disease or condition and its severity, the identity (e.g., weight) of the subject or host in need of treatment, but can nevertheless be determined in a manner recognized in the field according to the particular circumstances surrounding the case, including, e.g., the specific agent being administered, the route of administration, the condition being treated, and the subject or host being treated. In general, however, doses employed for adult human treatment will typically be in the range of about 0.02-about 5000 mg per day, in some embodiments, about 1-about 1500 mg per day. The desired dose may conveniently be presented in a single dose or as divided doses administered simultaneously (or over a short period of time) or at appropriate intervals, for example as two, three, four or more sub-doses per day.

The pharmaceutical composition described herein may be in unit dosage forms suitable for single administration of precise dosages. In unit dosage form, the formulation is divided into unit doses containing appropriate quantities of one or more compound. The unit dosage may be in the form of a package containing discrete quantities of the formulation. Non-limiting examples are packaged tablets or capsules, and powders in vials or ampoules. Aqueous suspension compositions can be packaged in single-dose non-reclosable containers. Alternatively, multiple-dose reclosable containers can be used, in which case it is typical to include a preservative in the composition. By way of example only, formulations for parenteral injection may be presented in unit dosage form, which include, but are not limited to ampoules, or in multi-dose containers, with an added preservative.

The daily dosages appropriate for the compounds described herein are from about 0.01 mg/kg to about 20 mg/kg. In one embodiment, the daily dosages are from about 0.1 mg/kg to about 10 mg/kg. An indicated daily dosage in the larger mammal, including, but not limited to, humans, is in the range from about 0.5 mg to about 1000 mg, conveniently administered in a single dose or in divided doses, including, but not limited to, up to four times a day or in extended release form. Suitable unit dosage forms for oral administration include from about 1 to about 500 mg active ingredient. In one embodiment, the unit dosage is about 1 mg, about 5 mg, about, 10 mg, about 20 mg, about 50 mg, about 100 mg, about 200 mg, about 250 mg, about 400 mg, or about 500 mg. The foregoing ranges are merely suggestive, as the number of variables in regard to an individual treatment regime is large, and considerable excursions from these recommended values are not uncommon. Such dosages may be altered depending on a number of variables, not limited to the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens can be determined by standard pharmaceutical procedures in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. The data obtained from cell culture assays and animal studies can be used in formulating a range of dosage for use in human. The dosage of such compounds lies preferably within a range of circulating concentrations that include the $ED_{50}$ with minimal toxicity. The dosage may vary within this range depending upon the dosage form employed and the route of administration utilized.

Combination Treatments

Compound 1 described herein, and compositions thereof, may also be used in combination with other therapeutic agents that are selected for their therapeutic value for the condition to be treated. In general, the compositions described herein and, in embodiments where combinational therapy is employed, other agents do not have to be administered in the same pharmaceutical composition, and may, because of different physical and chemical characteristics, have to be administered by different routes. The determination of the mode of administration and the advisability of administration, where possible, in the same pharmaceutical composition, is well within the knowledge of the clinician. The initial administration can be made according to established protocols recognized in the field, and then, based upon the observed effects, the dosage, modes of administration and times of administration can be modified by the clinician.

In certain instances, it may be appropriate to administer at least one compound described herein in combination with another therapeutic agent. By way of example only, if one of the side effects experienced by a patient upon receiving one of the compounds herein, such as Compound 1, is nausea, then it may be appropriate to administer an anti-nausea agent in combination with the initial therapeutic agent. Or, by way of example only, the therapeutic effectiveness of one of the compounds described herein may be enhanced by administration of an adjuvant (i.e., by itself the adjuvant may have minimal therapeutic benefit, but in combination with another therapeutic agent, the overall therapeutic benefit to the patient is enhanced). Or, by way of example only, the benefit experienced by a patient may be increased by administering one of the compounds described herein with another therapeutic agent (which also includes a therapeutic regimen) that also has therapeutic benefit. In any case, regardless of the disease, disorder, or condition being treated, the overall benefit experienced by the patient may simply be additive of the two therapeutic agents or the patient may experience a synergistic benefit.

In some embodiments, Compound 1 is administered in combination with an aminoglycoside antibiotic. In some embodiments, Compound 1 is administered in combination with an aminoglycoside antibiotic selected from streptomycin, neomycin, framycetin, paromomycin, paromomycin sulfate, ribostamycin, kanamycin, amikacin, arbekacin, bekanamycin, dibekacin, tobramycin, spectinomycin, hygromycin B, gentamicin, netilmicin, sisomicin, isepamicin, verdamicin, and astromicin. In some embodiments, Compound 1 is administered in combination with streptomycin. In some embodiments, Compound 1 is administered in combination with amikacin. In some embodiments, Compound 1 is administered in combination with neomycin. In some embodiments, Compound 1 is administered in combination with kanamycin. In some embodiments, Compound 1 is administered in combination with gentamicin. In some embodiments, Compound 1 is administered in combination with tobramycin.

In some embodiments, Compound 1 is administered for 1-7 days, and then Compound 1 is administered in combination with an aminoglycoside antibiotic. In some embodiments, Compound 1 is administered for 7 days, and then Compound 1 is administered in combination with an aminoglycoside antibiotic. In some embodiments, Compound 1 is administered for 6 days, and then Compound 1 is administered in combination with an aminoglycoside antibiotic. In some embodiments, Compound 1 is administered for 5 days, and then Compound 1 is administered in combination with an aminoglycoside antibiotic. In some embodiments, Compound 1 is administered for 4 days, and then Compound 1 is administered in combination with an aminoglycoside antibiotic. In some embodiments, Compound 1 is administered for 3 days, and then Compound 1 is administered in combination with an aminoglycoside antibiotic. In some embodiments, Compound 1 is administered for 2 days, and then Compound 1 is administered in combination with an aminoglycoside antibiotic. In some embodiments, Compound 1 is administered for 1 day, and then Compound 1 is administered in combination with an aminoglycoside antibiotic. In some embodiments, Compound 1 is administered an additional 7 days following the administration of the aminoglycoside antibiotic. In some embodiments, Compound 1 is administered an additional 6 days following the administration of the aminoglycoside antibiotic. In some embodiments, Compound 1 is administered an additional 5 days following the administration of the aminoglycoside antibiotic. In some embodiments, Compound 1 is administered an additional 4 days following the administration of the aminoglycoside antibiotic. In some embodiments, Compound 1 is administered an additional 3 days following the administration of the aminoglycoside antibiotic. In some embodiments, Compound 1 is administered an additional 2 days following the administration of the aminoglycoside antibiotic. In some embodiments, Compound 1 is administered an additional 1 day following the administration of the aminoglycoside antibiotic.

In some embodiments Compound 1 and the aminoglycoside antibiotic are administered in combination in a single dosage form. In some embodiments Compound 1 and the aminoglycoside antibiotic are administered in combination in separate dosage forms.

In some embodiments, Compound 1 is administered in combination with a chemotherapeutic agent. In some embodiments, Compound 1 is administered in combination with a chemotherapeutic agent selected from cisplatin and carboplatin. In some embodiments, Compound 1 is administered in combination with cisplatin. In some embodiments, Compound 1 is administered in combination with carboplatin.

The particular choice of compounds used will depend upon the diagnosis of the attending physicians and their judgment of the condition of the patient and the appropriate treatment protocol. The compounds may be administered concurrently (e.g., simultaneously, essentially simultaneously or within the same treatment protocol) or sequentially, depending upon the nature of the disease, disorder, or condition, the condition of the patient, and the actual choice of compounds used. The determination of the order of administration, and the number of repetitions of administration of each therapeutic agent during a treatment protocol, is well within the knowledge of the physician after evaluation of the disease being treated and the condition of the patient.

Therapeutically-effective dosages can vary when the drugs are used in treatment combinations. Methods for experimentally determining therapeutically-effective dosages of drugs and other agents for use in combination treatment regimens are described in the literature. For example, the use of metronomic dosing, i.e., providing more frequent, lower doses in order to minimize toxic side effects, has been described extensively in the literature. Combination treatment further includes periodic treatments that start and stop at various times to assist with the clinical management of the patient.

For combination therapies described herein, dosages of the co-administered compounds will of course vary depending on the type of co-drug employed, on the specific drug employed, on the disease or condition being treated and so forth. In addition, when co-administered with one or more biologically active agents, the compound provided herein may be administered either simultaneously with the biologically active agent(s), or sequentially. If administered sequentially, the attending physician will decide on the appropriate sequence of administering protein in combination with the biologically active agent(s).

In any case, the multiple therapeutic agents (one of which is Compound 1 described herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may vary from more than zero weeks to less than four weeks. In addition, the combination methods, compositions and formulations are not to be limited to the use of only two agents; the use of multiple therapeutic combinations are also envisioned.

The dosage regimen to treat, prevent, or ameliorate the condition(s) for which relief is sought, can be modified in accordance with a variety of factors. These factors include the disorder or condition from which the subject suffers, as well as the age, weight, sex, diet, and medical condition of the subject. Thus, the dosage regimen actually employed can vary widely and therefore can deviate from the dosage regimens set forth herein.

The pharmaceutical agents which make up the combination therapy disclosed herein may be a combined dosage form or in separate dosage forms intended for substantially simultaneous administration. The pharmaceutical agents that make up the combination therapy may also be administered sequentially, with either therapeutic compound being administered by a regimen calling for two-step administration. The two-step administration regimen may call for sequential administration of the active agents or spaced-apart administration of the separate active agents. The time period between the multiple administration steps may range from a few minutes to several hours, depending upon the properties of each pharmaceutical agent such as potency, solubility, bioavailability, plasma half-life and kinetic profile of the pharmaceutical agent. Circadian variation of the target molecule concentration may also determine the optimal dose interval.

In addition, the compounds described herein also may be used in combination with procedures that may provide additional or synergistic benefit to the patient. By way of example only, patients are expected to find therapeutic and/or prophylactic benefit in the methods described herein, wherein pharmaceutical composition of a compound disclosed herein and/or combinations with other therapeutics are combined with genetic testing to determine whether that individual is a carrier of a mutant gene that is correlated with certain diseases or conditions.

The compounds described herein and combination therapies can be administered before, during, or after the occurrence of a disease or condition, and the timing of administering the composition containing a compound can vary. Thus, for example, the compounds can be used as a prophylactic and can be administered continuously to subjects with a propensity to develop conditions or diseases in order to prevent the occurrence of the disease or condition. The initial administration can be via any route practical, such as, for example, an intravenous injection, a bolus injection, infusion over about 5 minutes to about 5 hours, a pill, a capsule, transdermal patch, buccal delivery, and the like, or combination thereof. A compound is preferably administered as soon as is practicable after the onset of a disease or condition is detected or suspected, and for a length of time necessary for the treatment of the disease or condition. The length of treatment can vary for each subject, and the length can be determined using specified criteria.

Kits/Articles of Manufacture

For use in the therapeutic methods of use described herein, kits and articles of manufacture are also described herein. Such kits include a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. In one embodiment, the containers are formed from a variety of materials such as glass or plastic.

The articles of manufacture provided herein contain packaging materials. Packaging materials for use in packaging pharmaceutical products include, e.g., U.S. Pat. No. 5,323, 907. Examples of pharmaceutical packaging materials include, but are not limited to, blister packs, bottles, tubes, bags, containers, bottles, and any packaging material suitable for a selected formulation and intended mode of administration and treatment.

In some embodiments, the compounds or compositions described herein, are presented in a package or dispenser device which may contain one or more unit dosage forms containing the active ingredient. The compound or composition described herein is packaged alone, or packaged with another compound or another ingredient or additive. In some embodiments, the package contains one or more containers filled with one or more of the ingredients of the pharmaceutical compositions. In some embodiments, the package comprises metal or plastic foil, such as a blister pack. In some embodiments, the package or dispenser device is accompanied by instructions for administration, such as instructions for administering the compounds or compositions for treating a neoplastic disease. In some embodiments, the package or dispenser is accompanied with a notice associated with the container in form prescribed by a governmental agency regulating the manufacture, use, or sale of pharmaceuticals, which notice is reflective of approval by the agency of the form of the drug for human or veterinary administration. In some embodiments, such notice, for example, is the labeling approved by the U.S. Food and Drug Administration for prescription drugs, or the approved product insert. In one embodiment, compositions include a compound described herein formulated in a compatible pharmaceutical carrier are prepared, placed in an appropriate container, and labeled for treatment of an indicated condition.

For example, the container(s) include Compound 1, optionally in a composition or in combination with another agent as disclosed herein. Such kits optionally include an identifying description or label or instructions relating to its use in the methods described herein.

A kit typically includes labels listing contents and/or instructions for use, and package inserts with instructions for use. A set of instructions will also typically be included.

In one embodiment, a label is on or associated with the container. In one embodiment, a label is on a container when letters, numbers or other characters forming the label are attached, molded or etched into the container itself; a label is associated with a container when it is present within a receptacle or carrier that also holds the container, e.g., as a package insert. In one embodiment, a label is used to indicate that the contents are to be used for a specific therapeutic application. The label also indicates directions for use of the contents, such as in the methods described herein.

In certain embodiments, the pharmaceutical compositions are presented in a pack or dispenser device which contains one or more unit dosage forms containing a compound provided herein. The pack, for example, contains metal or plastic foil, such as a blister pack. In one embodiment, the pack or dispenser device is accompanied by instructions for administration. In one embodiment, the pack or dispenser is also accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In one embodiment, compositions containing a compound provided herein formulated in a compatible pharmaceutical carrier are also prepared, placed in an appropriate container, and labeled for treatment of an indicated condition.

EXAMPLES

List of Abbreviations

As used throughout the description of the invention, the following abbreviations, unless otherwise indicated, shall be understood to have the following meanings:

ACN or MeCN acetonitrile
Bn benzyl
BOC or Boc tert-butyl carbamate
t-Bu tert-butyl
Cy cyclohexyl
DCE dichloroethane ($ClCH_2CH_2Cl$)
DCM dichloromethane ($CH_2Cl_2$)
DIPEA or DIEA diisopropylethylamine
DMAP 4-(N,N-dimethylamino)pyridine
DMF dimethylformamide
DMA N,N-dimethylacetamide
DMSO dimethylsulfoxide
eq or equiv equivalent(s)
Et ethyl
$Et_2O$ diethyl ether
EtOH ethanol
EtOAc ethyl acetate
HPLC high performance liquid chromatography Me methyl
MeOH methanol
MS mass spectroscopy
GC gas chromatography
h hour(s)
KF Karl Fischer
mesylate methanesulfonate
min minutes
MsOH methanesulfonic acid
NMR nuclear magnetic resonance
RP-HPLC reverse phase-high performance liquid chromatography
TFA trifluoroacetic acid
THF tetrahydrofuran
TLC thin layer chromatography I. Salt Screen A salt screen was performed using 24 different counter ions which are added in a 1:1 ratio to the free base (Compound B). The library design shown in Table 1. The solvents selected were water, methanol, acetonitrile, and ethyl acetate. For sulfonic acids, the solvent methanol was replaced by toluene to avoid the formation of any possible toxic sulfonate side-products.

TABLE 1

| Position | Counter ion |
| --- | --- |
| 2, 14, 26, 38 | D-glucuronic acid (D-Glc) |
| 3, 15, 27, 39 | D-gluconic acid (D-Glu) |
| 4, 16, 28, 40 | L-aspartic acid (L-Asp) |
| 5, 17, 29, 41 | Maleic acid (Mae) |
| 6, 18, 30, 42 | Glutamic acid (Glm) |
| 7, 19, 31, 43 | Glutaric acid (Glr) |
| 8, 20, 32, 44 | L-tartaric acid (L-Tar) |
| 9, 21, 33, 45 | Fumaric acid (Fum) |
| 10, 22, 34, 46 | Citric acid (Cit) |
| 11, 23, 35, 47 | Glycolic acid (Gly) |
| 12, 24, 36, 48 | L-malic acid (L-Mal) |
| 49, 61, 73, 85 | L-ascorbic (L-Asc) |
| 50, 62, 74, 86 | Succinic acid (Suc) |
| 51, 63, 75, 87 | Adipic acid (Adi) |
| 52, 64, 76, 88 | Acetic acid (Ace) |
| 53, 65, 77, 89 | Benzoic acid (Ben) |
| 54, 66, 78, 90 | Sulfuric acid (Sul) |
| 55, 67, 79, 91 | Phosphoric acid (Pho) |
| 56, 68, 80, 92 | Ethanesulfonic acid (Esy) |
| 57, 69, 81, 93 | Methanesulfonic acid (Mes) |
| 58, 70, 82, 94 | 1,2-ethanedisulfonic acid (Edi) |
| 59, 71, 83, 95 | P-toluenesulfonic acid (Tos) |
| 60, 72, 84, 96 | Benzenesulfonic acid (Bes) |

The master plate represents the series of slurry experiments which used a concentration of 25 mg/ml of Compound B and 1 equivalent of corresponding acid. This plate was slurried at 50° C. for 2 hours. 400 μL Aliquot of filtrate was transferred from the master plate to the cooling plate, using the hot filter plate. Remaining solvents were removed via wicking using filter paper and crystals allowed to dried in air. The cooling crystallization plate was cooled slowly from 50° C. to 10° C. over 8 hours using an inverse cubic rate. The plate was equilibrated for 2 hours at 10° C. The obtained solids were isolated by evaporation under vacuum conditions. All obtained solids were characterized by XRPD.

A ranking of the most suitable candidates for salt selection was made which was based on the crystallinity, the counterion ICH class, the color, and the crystal habit of the material. LC purity was measured of the top four salts and resulted in an improved purity compared to the initial material hydrochloride.

Scale up synthesis was performed for three salt selection candidates (edisylate, citrate, and acetate). These slurry experiments were performed at gram scale with 25 mg/ml Compound B in 20 mL solvent with 1 equivalent of each acid. Slurrying was continued at 50° C. for 2 hours. The mixtures were allowed to cool down to room temperature and were then filtered and allowed to dried in air. XRPD, NMR, TGA/DSC and LC was measured for all solids. The salt formation was confirmed for the edisylate salt using XRPD and NMR measurement. Citrate and Acetate were not easily scalable according to XRPD and NMR measurements. The edisylate salt showed improved in purity, with low residual solvent and a high melting event, according to LC and TGA/DSC measurements.

A further set of salts were selected to be scaled up: mesylate, tosylate, besylate and tartate. These slurry experiments were also performed at gram scale with 25 mg/mL Compound B in 20 mL ethyl acetate with 1 equivalent acid. The experiments resulted in the expected salts except for tartate, according to XRPD measurements. The solubility in water for the four salts was determined and are shown in Table 2.

TABLE 2

| Salt | Solubility (mg/mL) |
| --- | --- |
| HCl salt (reference point) | 9-31 |
| Mesylate | 97-970 |
| Tosylate | <0.1 |
| Besylate | <0.1 |
| Tartate | 1.5-3 |

The mesylate gave the best solubility results. DVS measurement was performed to determine the hygroscopicity and check whether the polymorphic form and crystallinity of the salts remained after the DVS measurement. The mesylate salt was slightly hygroscopic at high humidity levels and the crystallinity of the polymorph remained unchanged.

II. Chemical Synthesis

Unless otherwise noted, reagents and solvents were used as received from commercial suppliers. Anhydrous solvents and oven-dried glassware were used for synthetic transformations sensitive to moisture and/or oxygen. Yields were not optimized. Reaction times are approximate and were not optimized. Column chromatography and thin layer chromatography (TLC) were performed on silica gel unless otherwise noted.

Example 1: Preparation of (4R,7S)-2-(3-(4-chlorophenyl)ureido)-9-methyl-5,6,7,8-tetrahydro-4H-4,7-epiminocyclohepta[b]thiophene-3-carboxamide mesylate (Compound 1, methanesulfonate salt of (4R,7S)-2-(3-(4-chlorophenyl)ureido)-9-methyl-5,6,7,8-tetrahydro-4H-4,7-epiminocyclohepta[b]thiophene-3-carboxamide)

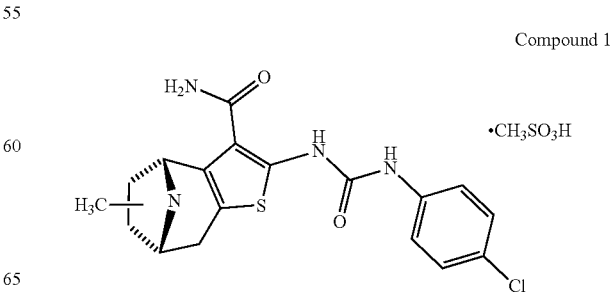

Compound 1

Step 1: (4R,7S)-2-amino-9-methyl-5,6,7,8-tetrahydro-4H-4,7-epiminocyclohepta-[b]thiophene-3-carboxamide (A)

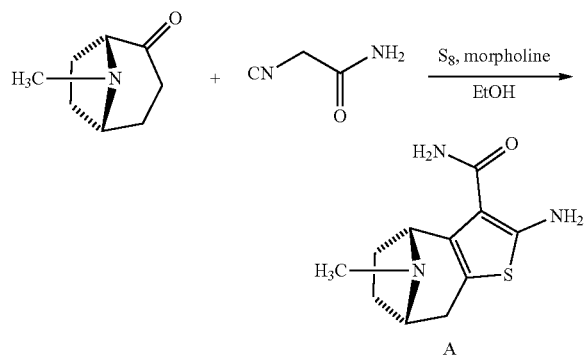

(1R)-2-Tropinone (1 eq) was charged to a mixture of cyanoacetamide (1.1 eq) and sulfur (1.2 eq) in ethanol (EtOH) (15 mL/g starting tropinone), followed by morpholine (0.5 eq). The reaction mixture was heated to 50° C. and stirred at that temperature for 60 h.

The reaction mixture was filtered at 15-30° C. to remove minor insolubles, the filter cake and filter medium were rinsed with EtOH (2 mL/g starting tropinone) and the combined filtrate was concentrated under reduced pressure and heating at ≤45° C. to a residual volume of 3.5 mL/g starting tropinone. Ethyl acetate (EtOAc) (10 mL/g starting tropinone) was charged to the concentrated residue at 25° C. over a minimum of 30 minutes (min). The resulting slurry was aged at 25° C. over a minimum of 1 h. The slurry was then chilled to −5° C. and aged at that temperature over a minimum of 1 h. The solids were collected by filtration. The filter cake was rinsed with two portions of EtOAc (3 mL/g starting tropinone per portion) and dried in a vacuum oven at 45° C. to yield Compound A (73%) as a brown solid.

Step 2: (4R,7S)-2-(3-(4-chlorophenyl)ureido)-9-methyl-5,6,7,8-tetrahydro-4H-4,7-epiminocyclohepta[b]thiophene-3-carboxamide hydrate (B)

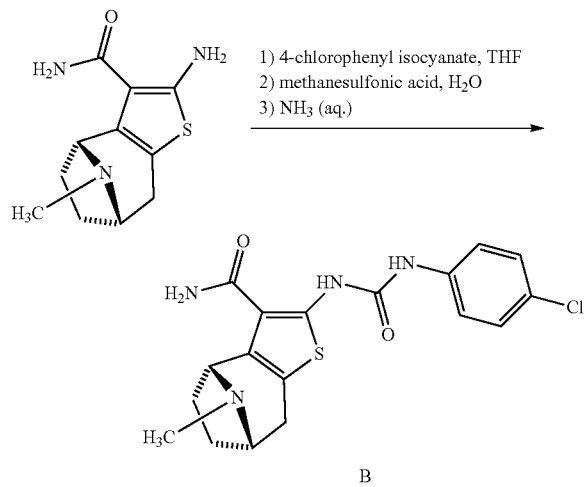

A solution of 4-chlorophenyl isocyanate (1.0 eq) in tetrahydrofuran (THF) (15 mL/g starting Compound A) was charged to a mixture of Compound A (1 eq) in THF (10 mL/g starting Compound A) at −5° C. over a minimum of 1 h. The reaction mixture was stirred at that temperature for 4 h.

Water (0.5 mL/g starting Compound A) was charged as a quench and the reaction mixture was concentrated under reduced pressure and at ≤30° C. to a residual volume of 5 mL/g starting Compound A. Water (18 mL/g starting Compound A) was charged to the concentrated residue. Methanesulfonic acid (MsOH) (0.85 eq) in water (2 mL/g MsOH) was charged to the resulting slurry at 20° C. over 5 min. The resulting mixture was stirred at 20° C. for 5 min. The mixture was filtered and the filter cake was rinsed with a mixture of water (2.5 mL/g starting compound A) and THF (0.5 mL/g starting compound A). Aqueous ammonia (3 eq relative to starting compound A) was charged to the combined filtrate at 20° C. over 15 min. The resulting slurry was aged at that temperature over 1 h and the resulting solids were collected by filtration. The filter cake was rinsed twice with a mixture of water (5 mL/g starting compound A, each portion) and THF (1 mL/g starting compound A, each portion) and dried under reduced pressure at 50° C. for 12 h to yield Compound B (88%) as an off-white solid.

Step 3: (4R,7S)-2-(3-(4-chlorophenyl)ureido)-9-methyl-5,6,7,8-tetrahydro-4H-4,7-epiminocyclohepta[b]thiophene-3-carboxamide mesylate (Compound 1)

A solution of methanesulfonic acid (MsOH) (1 eq) in acetonitrile (ACN) (3 mL/g starting Compound B) was charged to a slurry of Compound B in ACN (15 mL/g starting Compound B) at 40° C. over 2 h. The resulting slurry was aged at that temperature over 1 h. The solids were collected by filtration. The filter cake was rinsed with two portions of ACN (5 mL/g starting Compound B per portion) and dried under reduced pressure at 45° C. for 12 h to yield Compound 1 (85%) as an off-white solid.

III. Characterization of Compounds

Example 2: X-Ray Powder Diffraction (XRPD)

X-ray powder diffraction studies were performed using a Bruker AXS D2 PHASER in Bragg-Brentano configuration. Operating conditions: Cu anode at 30 kV, 10 mA; sample stage standard rotating; monochromatisation by a Kβ-filter (0.5% Ni). Slits: fixed divergence slits 1.0 mm (=0.61°), primary axial Soller slit 2.5°, secondary axial Soller slit 2.5°. Detector: Linear detector LYNXEYE with receiving slit 5° detector opening. The standard sample holder (0.1 mm cavity in (510) silicon wafer) has a minimal contribution to the background signal.

Measurement conditions: scan range 5-45° 2θ, sample rotation 5 rpm, 0.5 s/step, 0.010°/step, 3.0 mm detector slit; all measurement conditions are logged to an instrument control file. As system suitability, a corundum sample A26-B26-S (NIST standard) was measured daily.

Data collection was performed using Diffrac.Commander v2.0.26 software. Data analysis was performed using Diffrac.Eva v1.4 software. No background correction or smoothing was applied to the patterns.

XRPD analysis (FIG. 1) of Compound 1 showed the mesylate salt to be crystalline. The peaks displayed in the diffraction pattern of FIG. 1 are tabulated in Table 3 where the column headings have the following meanings: 1) 2-Theta, 2θ in degrees; 2) d(Å), d-spacing in Å, based on wavelength=1.54059 Å (Cu/K-alpha1); 3) Height, counts per second; 4) H %, height, relative percent; 5) Area; 6) A %, area, relative percent; and 7) FWHM, full width at half maximum.

TABLE 3

| 2-Theta | d(Å) | Height | H % | Area | A % | FWHM |
|---|---|---|---|---|---|---|
| 7.593 | 11.6342 | 4091 | 68.6 | 20165 | 61.9 | 0.209 |
| 9.391 | 9.4104 | 293 | 4.9 | 1573 | 4.8 | 0.228 |
| 10.648 | 8.3014 | 1206 | 20.2 | 6569 | 20.2 | 0.231 |
| 11.995 | 7.3721 | 275 | 4.6 | 1036 | 3.2 | 0.160 |
| 13.432 | 6.5865 | 197 | 3.3 | 1058 | 3.3 | 0.228 |
| 15.008 | 5.8984 | 5722 | 96.0 | 25782 | 79.2 | 0.191 |
| 15.992 | 5.5375 | 1719 | 28.8 | 7257 | 22.3 | 0.179 |
| 16.782 | 5.2787 | 1705 | 28.6 | 6535 | 20.1 | 0.163 |
| 17.652 | 5.0204 | 2413 | 40.5 | 11335 | 34.8 | 0.200 |
| 18.276 | 4.8503 | 76 | 1.3 | 312 | 1.0 | 0.165 |
| 18.664 | 4.7503 | 126 | 2.1 | 284 | 0.9 | 0.096 |
| 19.802 | 4.4798 | 190 | 3.2 | 1642 | 5.0 | 0.345 |
| 20.100 | 4.4142 | 699 | 11.7 | 4503 | 13.8 | 0.274 |
| 21.206 | 4.1864 | 382 | 6.4 | 1993 | 6.1 | 0.222 |
| 21.908 | 4.0537 | 5962 | 100.0 | 32552 | 100.0 | 0.232 |
| 22.492 | 3.9498 | 1963 | 32.9 | 8718 | 26.8 | 0.189 |
| 23.167 | 3.8362 | 440 | 7.4 | 382 | 1.2 | 0.050 |
| 23.660 | 3.7574 | 260 | 4.4 | 2681 | 8.2 | 0.412 |
| 23.944 | 3.7134 | 277 | 4.6 | 2095 | 6.4 | 0.321 |
| 24.355 | 3.6517 | 879 | 14.7 | 4818 | 14.8 | 0.233 |
| 25.089 | 3.5465 | 92 | 1.5 | 298 | 0.9 | 0.138 |
| 26.219 | 3.3962 | 263 | 4.4 | 853 | 2.6 | 0.138 |
| 27.036 | 3.2954 | 432 | 7.3 | 1743 | 5.4 | 0.171 |
| 27.649 | 3.2237 | 1196 | 20.1 | 7944 | 24.4 | 0.282 |
| 27.831 | 3.2030 | 441 | 7.4 | 3007 | 9.2 | 0.273 |
| 28.853 | 3.0918 | 219 | 3.7 | 2458 | 7.6 | 0.478 |
| 29.293 | 3.0464 | 417 | 7.0 | 3366 | 10.3 | 0.343 |
| 31.542 | 2.8342 | 471 | 7.9 | 2556 | 7.9 | 0.231 |
| 32.007 | 2.7940 | 270 | 4.5 | 2480 | 7.6 | 0.391 |
| 32.445 | 2.7573 | 263 | 4.4 | 2611 | 8.0 | 0.422 |
| 32.988 | 2.7131 | 109 | 1.8 | 283 | 0.9 | 0.111 |
| 33.749 | 2.6537 | 472 | 7.9 | 3238 | 9.9 | 0.292 |
| 34.501 | 2.5975 | 195 | 3.3 | 948 | 2.9 | 0.207 |
| 35.210 | 2.5469 | 137 | 2.3 | 772 | 2.4 | 0.240 |
| 35.996 | 2.4930 | 93 | 1.6 | 346 | 1.1 | 0.158 |
| 36.793 | 2.4408 | 210 | 3.5 | 751 | 2.3 | 0.152 |
| 37.741 | 2.3816 | 156 | 2.6 | 1019 | 3.1 | 0.278 |
| 38.343 | 2.3456 | 197 | 3.3 | 1325 | 4.1 | 0.286 |
| 39.051 | 2.3047 | 73 | 1.2 | 481 | 1.5 | 0.262 |
| 39.458 | 2.2818 | 122 | 2.0 | 741 | 2.3 | 0.244 |

Example 3: Polarized Light Microscopy (PLM)

Light microscopy studies were performed using an AxioVert 35M, equipped with an AxioCamERc 5s. The microscope was equipped with four lenses: Zeiss A-Plan 5×/0.12, Zeiss A-Plan 10×/0.25, LD A-Plan 20×/0.30 and Achros TIGMAT 32×/0.40. Data collection and evaluation was performed using Carl Zeiss Zen AxioVision Blue Edition Lite 2011 v1.0.0.0 software. A small amount of sample was loaded on an object glass and carefully spread until a thin layer was obtained.

PLM analysis of Compound 1 showed a white powder consisting of fines and plates, less than 20 μm.

Example 4: Thermogravimetric Analysis/Differential Scanning Calorimetry (TGA/DSC)

Combined TGA/DSC studies were performed using a Mettler Toledo TGA/DSC1 STARe System, equipped with an auto-sampler, and using pin-holed (pierced) aluminum crucibles of 40 μl. Measurement conditions: 5 min 30.0° C., 30.0-350.0° C. with 10° C./min., nitrogen flow of 40 mL/min. Instrument control and data analysis were performed using STARe v15.00 software.

In the combined TGA/DSC thermogram of Compound 1 (FIG. 2), the TGA showed a mass loss of 19.5% on melting, and separate from onset of degradation. The DSC showed a single endotherm with an onset temperature at about 199° C. and a peak (melting point) at about 202° C. (reported as 198.79 and 201.94° C., respectively).

Example 5: Differential Scanning Calorimetry (DSC)

DSC studies were performed using a Mettler Toledo DSC1 or DSC2 STARe System. The samples were prepared using pre-weighed aluminum crucibles (40 μl; pierced), typically loaded with 1-8 mg of sample, and analyzed under the following temperature programs: maintained at 30° C. for 5 minutes, heated at 10° C./min from 30° C. to 350° C., and maintained at 350° C. for 1 minute (DSC1); heated at 10° C./min from 30° C. to 300° C. (DSC2). A nitrogen purge of 40 ml/min was maintained over the sample. As system suitability check, indium and zinc were used as references. Data collection and evaluation were performed using STARe Software v12.10 or v15.00 (DSC1), or v14.00 (DSC2). No corrections were applied to the thermograms.

DSC results for three samples of crystalline Compound 1 are summarized in Table 4.

TABLE 4

| Sample | Instrument | Software version | Melt Onset | Melt Peak |
|---|---|---|---|---|
| A | DSC1 | 12.10 | 203.00° C. | 205.02° C. |
| B | DSC2 | 14.00 | 205.14° C. | 206.22° C. |
| C | DSC1 | 15.00 | 199.45° C. | 202.35° C. |

Example 6: Dynamic Vapor Sorption (DVS)

DVS studies were performed using a Surface Measurement Systems Ltd. DVS-1 No Video. The sample, typically 20-30 mg, was loaded into a balance pan and equilibrated at 0% relative humidity (RH). After the material was dried, the RH was increased at 10% per step for 1 hour per increment, ending at 95% RH. After completion of the sorption cycle, the sample was dried using the same method, and the cycle was repeated. The software used for data collection was DVSWin v3.01 No Video. Data analysis was performed using DVS Standard Analysis Suite v6.3.0 (Standard).

Figure 3:
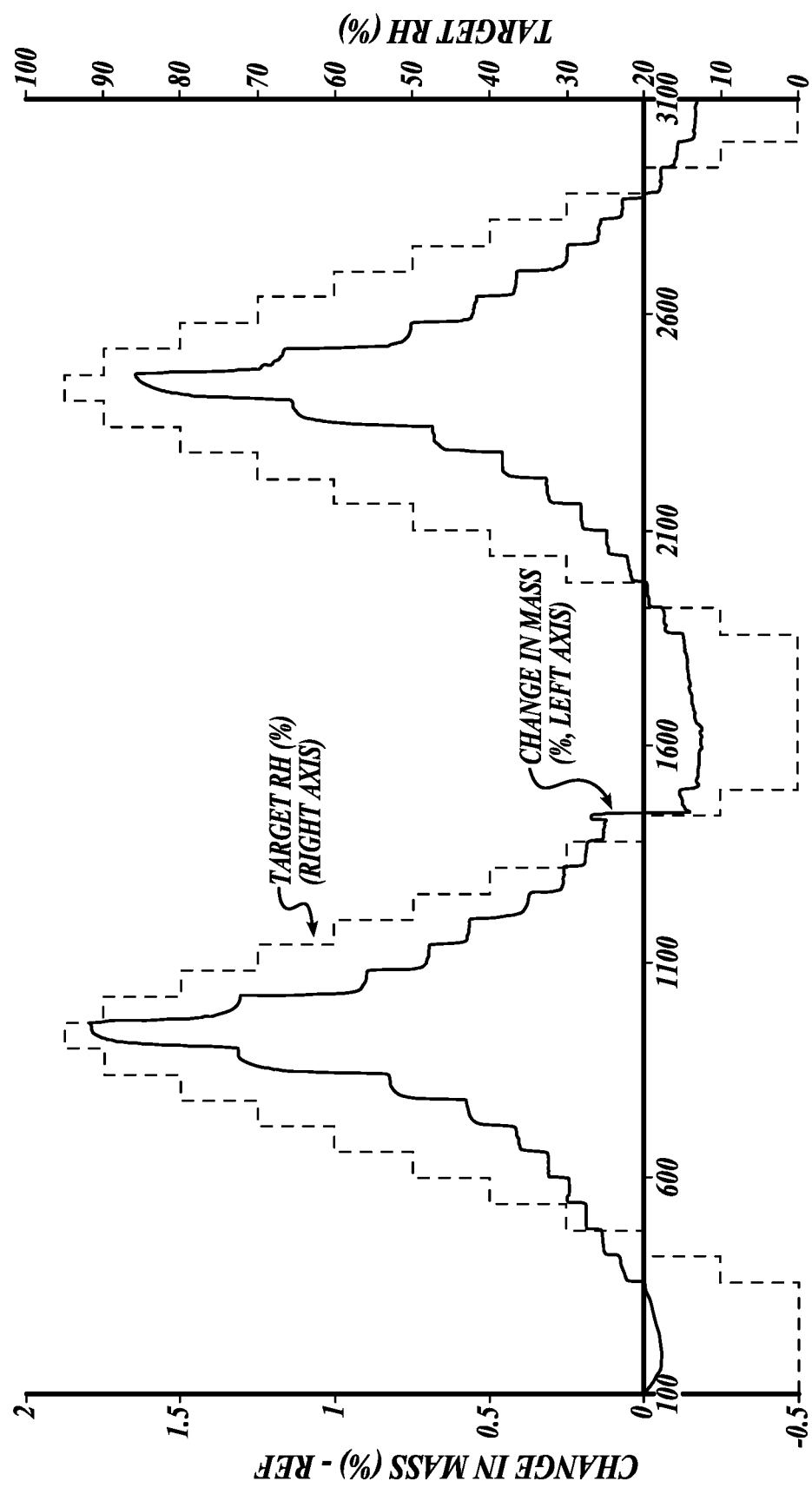
FIG. 3. Illustrates the result of a dynamic vapor sorption (DVS) study of crystalline (4R,7S)-2-(3-(4-chlorophenyl)ureido)-9-methyl-5,6,7,8-tetrahydro-4H-4,7-epiminocyclohepta[b]thiophene-3-carboxamide mesylate salt.

The DVS analysis of Compound 1 (FIG. 3) showed stepwise sorption in response to changes in RH with a total mass uptake of 1.8% in the first sorption cycle, and 1.6% in the second cycle. The material is slightly hygroscopic.

Figure 4:
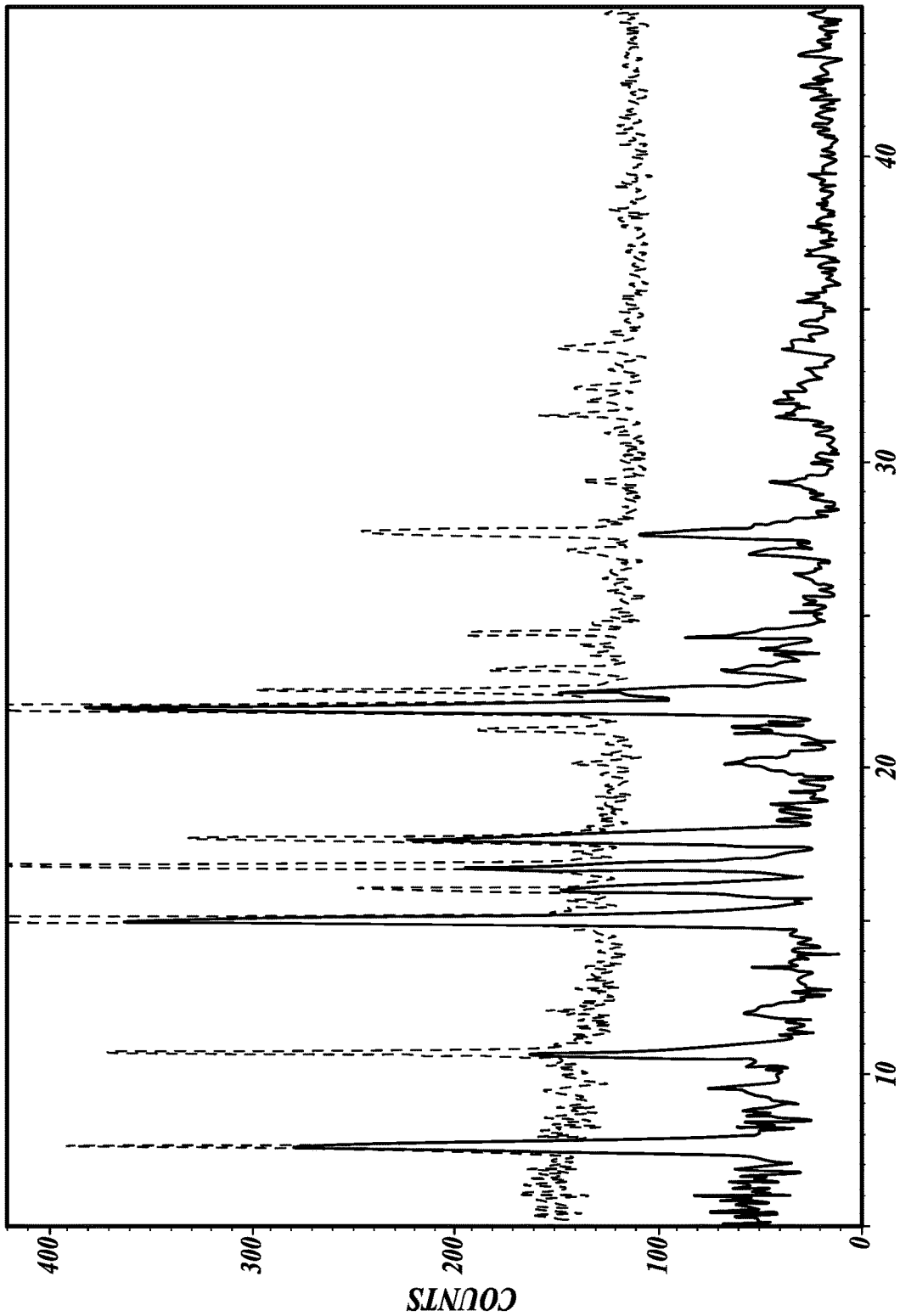
FIG. 4. Illustrates X-ray powder diffraction (XRPD) patterns of crystalline (4R,7S)-2-(3-(4-chlorophenyl)ureido)-9-methyl-5,6,7,8-tetrahydro-4H-4,7-epiminocyclohepta[b]thiophene-3-carboxamide mesylate salt before and after DVS analysis (top pattern=before DVS, bottom pattern=after DVS).

XRPD patterns recorded before and after DVS analysis (FIG. 4, top pattern=before DVS, bottom pattern=after DVS) showed the material was unchanged by exposure to these cycles of relative humidity.

Example 7: Infrared Spectroscopy (IR)

The FT-IR studies were performed using a Thermo Scientific Nicolet iS50. An attenuated total reflectance (ATR) technique was used with a beamsplitter of KBr. Measurement conditions: number of scans, 16; resolution, 4 cm$^{-1}$; data collected from 400 cm$^{-1}$ to 4000 cm$^{-1}$. The software OMNIC version 9.2 was used for data collection and evaluation.

IR analysis of Compound 1 is shown in FIG. 5.

Example 8: $^1$H Nuclear Magnetic Resonance ($^1$H NMR)

$^1$H-NMR studies were performed using an Agilent Inova400 (frequency: 400 MHz). Compound 1 was dissolved in deuterated DMSO and chemical shifts (δ ppm) were reported relative to internal tetramethylsilane (δ 0.00 ppm).

Figure 6:
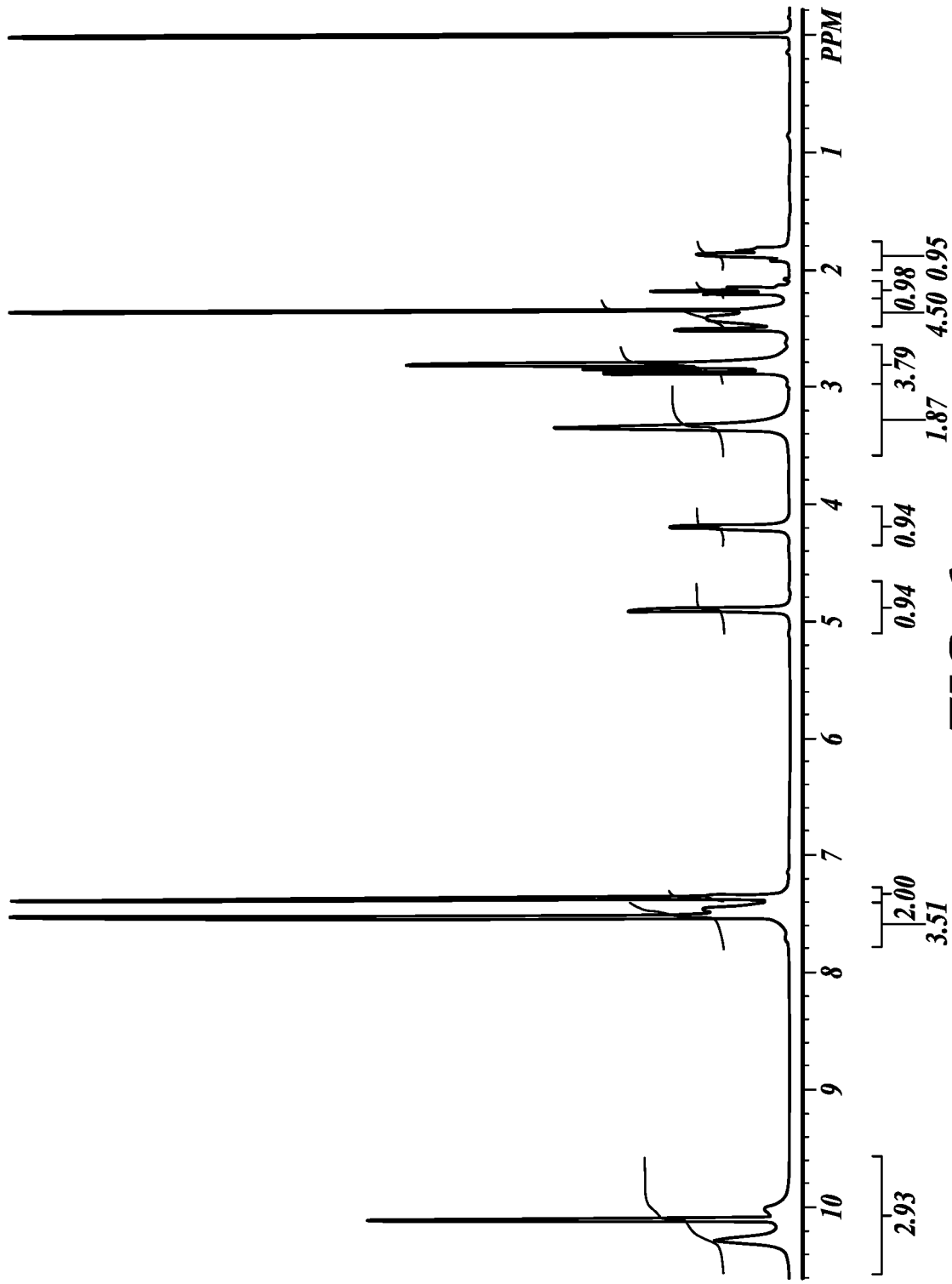
FIG. 6. Illustrates an $^1$H NMR spectrum of (4R,7S)-2-(3-(4-chlorophenyl)ureido)-9-methyl-5,6,7,8-tetrahydro-4H-4,7-epiminocyclohepta[b]thiophene-3-carboxamide mesylate salt.

The $^1$H NMR spectrum of Compound 1 is shown in FIG. 6. $^1$H NMR (400 MHz, DMSO-d$_6$) δ 10.28 (br s, 1H), 10.09 (s, 1H), 9.98 (br s, 1H), 7.50 (d, J=9.0 Hz, 2H), 7.45 (br s, 1H), 7.35 (d, J=9.0 Hz, 2H), 4.90 (br s, 1H), 4.19 (br s, 1H), 3.33 (m, 2H), 2.84 (m, 4H), 2.42 (m, 2H), 2.32 (s, 3H), 2.15 (m, 1H), 1.87 (m, 1H).

Example 9: High Performance Liquid Chromatography (HPLC)

HPLC was carried out using the following equipment and operating parameters:

Instrument: HPLC—Agilent 1100 (data were collected and evaluated using Agilent ChemStation for LC Systems Rev. B.04.02[96] software)

Column: Agilent Zorbax SB-C18, 5 μm particle size, 150 mm×4.6 mm

Column Temperature: 20.0±0.8° C.

Detector: Agilent 1100, type DAD G1315B, at 245 nm

Injection Volume: 5 μL (of 1 mg Compound 1/mL of water)

Flow Rate: 1 mL/min

Mobile Phase A: 0.1% trifluoroacetic acid in acetonitrile

Mobile Phase B: 0.1% trifluoroacetic acid in water

Gradient Program

| Time (min) | Mobile phase: A (v/v %), balance B |
|---|---|
| 0 | 95 |
| 9 | 5 |
| 10 | 95 |
| 14 | 95 |

Figure 7:
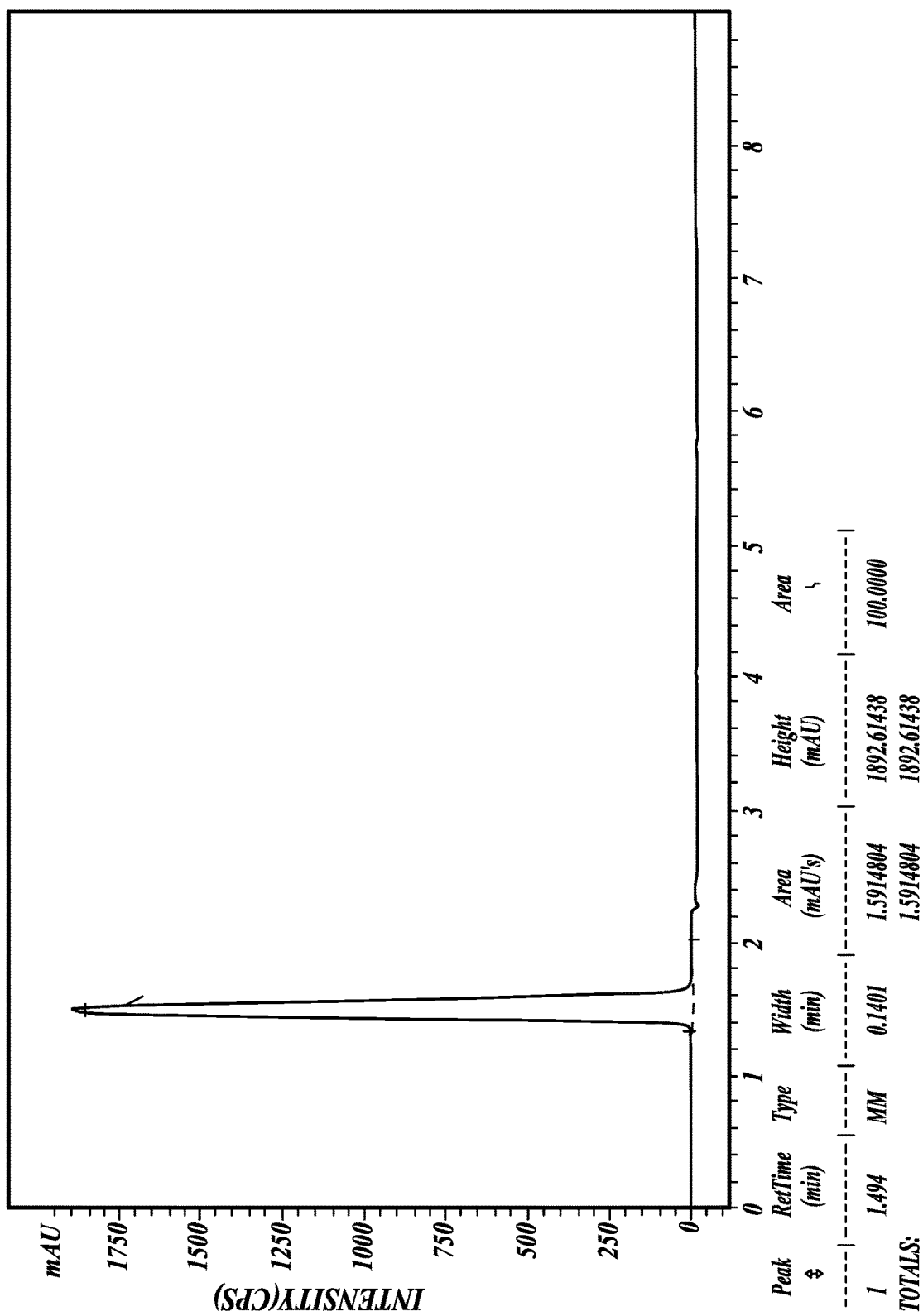
FIG. 7. Illustrates an HPLC chromatogram of (4R,7S)-2-(3-(4-chlorophenyl)ureido)-9-methyl-5,6,7,8-tetrahydro-4H-4,7-epiminocyclohepta[b]thiophene-3-carboxamide mesylate salt.

HPLC purity of Compound 1 was measured to be >99.9% (FIG. 7).

Example 10: Polarimetry

Optical rotation was measured using an Anton Paar Polarimeter. The Anton Paar Polarimeter was used under the following parameters: cell length of 100.00 mm; wavelength in air is 589.28 nm; wavelength in vacuum is 589.44 nm; set temperature is 20° C. To confirm system suitability, a quartz check is measured daily.

Duplicate measurement under these conditions and in DMSO solvent reported specific rotations of +19.6 and +20.4°.

Example 11: Liquid Chromatography—Mass Spectroscopy (LC-MS)

Liquid chromatogram mass loss measurements were performed using a Bruker MaXis QTOF and the following chemicals/supplies: water (UHPLC-MS grade), methanol (UHPLC-MS grade), acetonitrile (UHPLC-MS grade) and formic acid (HPLC grade). The sample was analyzed by direct infusion. ESI was used for ionization, and the spectra were recorded in positive mode over the mass range 50-1500 m/z. The mass spectrometer was calibrated internally using a calibration solution (sodium formate clusters in Mili-Q water).

Figure 8:
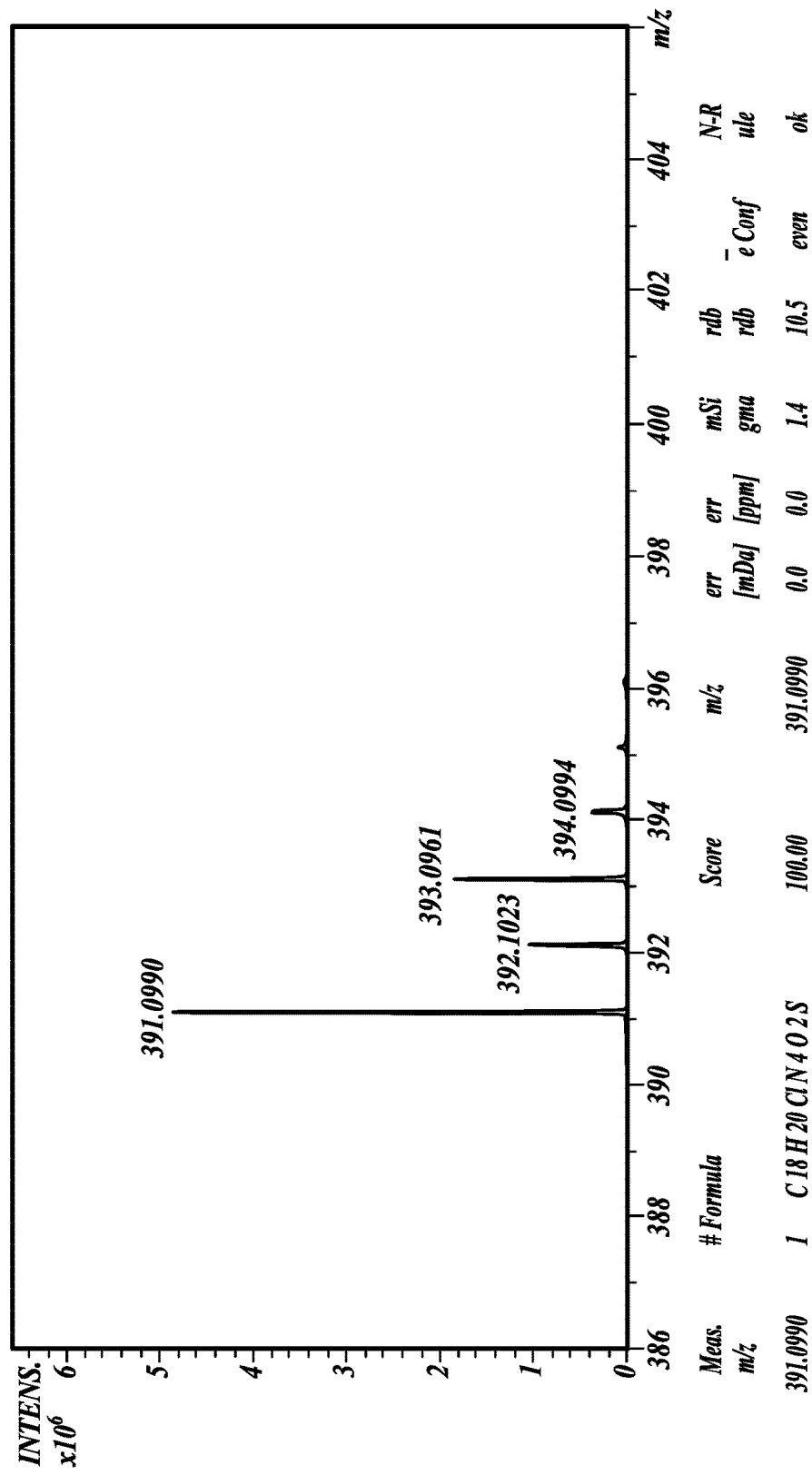
FIG. 8. Illustrates a high-resolution mass spectrum of the cation present in (4R,7S)-2-(3-(4-chlorophenyl)ureido)-9-methyl-5,6,7,8-tetrahydro-4H-4,7-epiminocyclohepta[b]thiophene-3-carboxamide mesylate salt.

The exact mass of the fragment corresponding to the protonated free base, i.e. the cation present in the mesylate salt, Compound 1, was determined to be 391.0990 (FIG. 8).

Example 12: Polymorph Screen of Compound 1

Polymorph screen experiments were performed on an Avantium Crystal 16™ parallel crystallizer. This instrument uses laser transmission for dissolution detection.

A polymorph screen of the mesylate salt was performed to determine stability and polymorphic behavior. Eight different solvents were investigated: toluene, water, acetonitrile, acetone, tert-butyl methyl ether, 2-butanone, isopropyl acetate and 2-methyltetrahydrofuran. The concentration was 25 mg/mL (on a free base basis) in 800 μL solvent. Slurry crystallization experiments were stirred overnight at room temperature. The protocol for cooling crystallization experiments was: heat to 50° C., cool to 10° C. using a cooling rate of 5° C. per hour. All eight solvents were tested in both slurry crystallization and cooling crystallization experiments. The recovered solids were characterized by XRPD.

Example 13: Solubility of Compound 1

The solubility was determined using the shake-flask method, where the solubility was visually determined at 20° C. Water was added stepwise to 10 mg of Compound 1, with 15 minutes in between additions, until complete dissolution was obtained.

The solubility of Compound 1 in water was found to be >97 mg/mL.

We claim:

1. A crystalline form of a mesylate salt of (4R,7S)-2-(3-(4-chlorophenyl)ureido)-9-methyl-5,6,7,8-tetrahydro-4H-4,7-epiminocyclohepta[b]thiophene-3-carboxamide, wherein the mesylate salt has an X-ray powder diffraction (XRPD) pattern with characteristic peaks at 7.6° 2-Theta, 10.6° 2-Theta, 15.0° 2-Theta, 16.0° 2-Theta, 16.8° 2-Theta, 17.7° 2-Theta, 21.9° 2-Theta, and 22.5° 2-Theta.

2. The crystalline form of claim 1, wherein the crystalline form is unsolvated.

3. The crystalline form of claim 1, wherein the crystalline form is anhydrous.

4. A pharmaceutical composition comprising the crystalline form of claim 1, and at least one inactive ingredient selected from pharmaceutically acceptable carriers, diluents, and excipients.

5. The pharmaceutical composition of claim 4 further comprising an aminoglycoside antibiotic.

6. The pharmaceutical composition of claim 5 wherein the aminoglycoside antibiotic is selected from streptomycin, neomycin, framycetin, paromomycin, paromomycin sulfate, ribostamycin, kanamycin, amikacin, arbekacin, bekanamycin, dibekacin, tobramycin, spectinomycin, hygromycin B, gentamicin, netilmicin, sisomicin, isepamicin, verdamicin, and astromicin.

7. A method for protecting against kidney damage in an individual receiving an aminoglycoside antibiotic comprising administering to the individual a therapeutically effective amount of a crystalline form of claim 1.

8. A method for treating hearing loss in an individual comprising administering to the individual a therapeutically effective amount of a crystalline form of claim 1.

9. A method for treating sensory hair cell death in an individual comprising administering to the individual a therapeutically effective amount of a crystalline form of claim 1.

10. The method of claim 8 wherein the hearing loss is associated with exposure to an ototoxic agent.

11. The method of claim 9 wherein the sensory hair cell death is associated with exposure to an ototoxic agent.

12. The method of claim 10 wherein the ototoxic agent is an aminoglycoside antibiotic, chemotherapeutic agent, loop diuretic, antimalarial sesquiterpene lactone endoperoxide, antimalarial quinine, salicylate, or interferon polypeptide.

13. The method of claim 7, wherein the aminoglycoside antibiotic is selected from streptomycin, neomycin, framycetin, paromomycin, paromomycin sulfate, ribostamycin, kanamycin, amikacin, arbekacin, bekanamycin, dibekacin, tobramycin, spectinomycin, hygromycin B, gentamicin, netilmicin, sisomicin, isepamicin, verdamicin, and astromicin.

14. The method of claim 12, wherein the aminoglycoside antibiotic is selected from streptomycin, neomycin, framycetin, paromomycin, paromomycin sulfate, ribostamycin, kanamycin, amikacin, arbekacin, bekanamycin, dibekacin, tobramycin, spectinomycin, hygromycin B, gentamicin, netilmicin, sisomicin, isepamicin, verdamicin, and astromicin.

15. The method of claim 11 wherein the ototoxic agent is an aminoglycoside antibiotic, chemotherapeutic agent, loop diuretic, antimalarial sesquiterpene lactone endoperoxide, antimalarial quinine, salicylate, or interferon polypeptide.

16. The method of claim 15, wherein the aminoglycoside antibiotic is selected from streptomycin, neomycin, framycetin, paromomycin, paromomycin sulfate, ribostamycin, kanamycin, amikacin, arbekacin, bekanamycin, dibekacin, tobramycin, spectinomycin, hygromycin B, gentamicin, netilmicin, sisomicin, isepamicin, verdamicin, and astromicin.

* * * * *